(12) United States Patent
Iyer et al.

(10) Patent No.: US 8,071,681 B2
(45) Date of Patent: Dec. 6, 2011

(54) POLYMERIC COMPOSITIONS INCLUDING THEIR USES AND METHODS OF PRODUCTION

(75) Inventors: Srivatsan Srinivas Iyer, Pearland, TX (US); Sudhin Datta, Houston, TX (US); Trazollah Ouhadi, Liege (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 945 days.

(21) Appl. No.: 11/632,741

(22) PCT Filed: Jul. 20, 2005

(86) PCT No.: PCT/US2005/025682
§ 371 (c)(1),
(2), (4) Date: Jan. 18, 2007

(87) PCT Pub. No.: WO2006/020309
PCT Pub. Date: Feb. 23, 2006

(65) Prior Publication Data
US 2007/0240605 A1    Oct. 18, 2007

Related U.S. Application Data

(60) Provisional application No. 60/601,467, filed on Aug. 13, 2004.

(51) Int. Cl.
*C08L 47/00* (2006.01)
*C08L 33/02* (2006.01)
*B32B 9/00* (2006.01)

(52) U.S. Cl. ............ 525/98; 525/97; 525/191; 525/221; 525/222; 525/95; 428/318.4; 428/319.3; 428/319.7; 428/319.9

(58) Field of Classification Search .................. 525/191, 525/221, 222, 98, 240; 428/318.4, 319.3, 428/319.7, 319.9
See application file for complete search history.

(56) References Cited

U.S. PATENT DOCUMENTS

| | | | |
|---|---|---|---|
| 4,775,711 A | 10/1988 | Kawamura et al. | 524/232 |
| 5,476,914 A | 12/1995 | Ewen et al. | |
| 5,885,908 A | 3/1999 | Jaeger et al. | 442/59 |
| 6,541,568 B1 * | 4/2003 | Ding et al. | 525/88 |
| 6,642,316 B1 | 11/2003 | Datta et al. | 525/240 |
| 7,557,162 B2 * | 7/2009 | Patel et al. | 525/191 |
| 2002/0122953 A1 | 9/2002 | Zhou | 428/517 |
| 2003/0022975 A1 | 1/2003 | Park et al. | 524/423 |
| 2003/0204017 A1 * | 10/2003 | Stevens et al. | 525/53 |
| 2004/0097650 A1 * | 5/2004 | Ogawa et al. | 525/98 |

FOREIGN PATENT DOCUMENTS

| | | |
|---|---|---|
| EP | 0 241 667 | 10/1987 |
| EP | 0 499 472 | 8/1992 |
| EP | 0 921 151 | 6/1999 |
| JP | 07138430 A * | 5/1995 |
| JP | 2000 129027 | 5/2000 |
| JP | 2000-191862 | 7/2000 |
| JP | 2004-149553 | 5/2004 |
| JP | 2004 338289 | 12/2004 |
| WO | WO 00/78862 | 12/2000 |
| WO | WO 02/083754 | 10/2002 |
| WO | WO 02081570 * | 10/2002 |
| WO | WO 2004/014998 | 2/2004 |
| WO | WO 2004/039907 | 5/2004 |

* cited by examiner

*Primary Examiner* — Jennifer Chriss
*Assistant Examiner* — Ricardo Lopez

(57) ABSTRACT

Polymeric compositions and methods of making and using such compositions are provided. The compositions incorporate at least one component that is a polymer including propylene-derived units and at least one component that is a styrenic block copolymer. The polymeric compositions are found to have desirable elastomeric properties while at the same time exhibiting beneficial processability characteristics. The unique combination of processability and performance attributes result in the polymeric compositions useful in a variety of applications such as films, fibers, woven and non-woven fabrics, sheets, molded objects, extruded forms, thermoformed objects, and all products made from such application materials.

50 Claims, No Drawings

POLYMERIC COMPOSITIONS INCLUDING THEIR USES AND METHODS OF PRODUCTION

CROSS REFERENCE TO RELATED APPLICATIONS

This application is a 371 National Stage Application of International Application No. PCT/US2005/025682, filed Jul. 20, 2005, which claims the benefit of Provisional Application No. 60/601,467, filed Aug. 13, 2004, the disclosures of which are herein incorporated by reference in their entireties.

FIELD OF THE DISCLOSURE

The disclosure relates to polymeric compositions and methods of making and using such compositions. The compositions incorporate at least one polymer including propylene-derived units and at least one styrenic block copolymer.

BACKGROUND INFORMATION

It is known to blend two or more polymeric materials to achieve beneficial performance characteristics in the resulting polymeric composition. One such conventional blending process is the blending of elastomeric and thermoplastic polymeric materials. For example, as described in U.S. Pat. No. 6,642,316, it is known to blend ethylene propylene based interpolymers with polypropylene so as to provide a polypropylene dispersed phase and an elastomeric continuous matrix phase. The overall blend may be elastomeric in nature. The ethylene propylene based interpolymers may be of the type described in WO 02/083754.

It is also known to blend an inverse distribution of phases, where the continuous matrix phase is a polypropylene and the dispersed is an ethylene propylene based interpolymer. The blends of this type are often referred to as TPO's (Thermoplastic Polyolefins). The dispersed phase acts as an impact modifier and improves the impact strength of the original polypropylene.

It is known to provide soft or softened resilient articles using styrenic block copolymers ("SBC's"). The SBC's may have a variety of hardness levels, expressed generally in Shore A. Generally elastomeric SBC's exhibit poor processability, limiting production capacity. For example, during continuous extrusion of SBC's for production of fibers or films, and the like, the extrudate may experience melt fracture, and therefore, may limit production line speeds.

WO 04/014998 discloses blends of polypropylene impact copolymers and SBC's. These blends also incorporate non-functionalized plasticizers.

U.S. Patent Application 2003/022975 discloses a blend of a highly crystalline isotactic polypropylene ethylene copolymer with a polyolefin elastomer, which may be a hydrogenated SBC. The compositions are described as having excellent rigidity and do not provide an elastic composition. U.S. Pat. No. 4,775,711 discloses elastomeric molding compositions that are blends of crystalline propylene-ethylene copolymers with block copolymers. EP 0 921 151 discloses compositions that are crosslinked blends of ethylene-alpha olefin copolymers and block copolymers. The blends are said to be useful for molding medical articles.

WO 2004/039907 discloses a hot melt adhesive incorporating up to 40 wt. % of a SBC, 4 wt. % to 50 wt. % of an RCP copolymer, and from 20 wt. % to 65 wt % of a tackifier. U.S. Patent Application 2002/0122953 discloses an elastic adhesive composition of a rubber-based adhesive, which may be a SBC and a semicrystalline polymer.

Other background references include U.S. Pat. No. 5,885,908, EP 0 241 667 A, EP 0 499 472 A, JP 2000 129027 A and JP 2004 338289 A.

SUMMARY OF THE DISCLOSURE

The disclosure relates to polymeric compositions and methods of making and using such compositions. The compositions incorporate at least one component that is a polymer including propylene-derived units and at least one component that is a styrenic block copolymer. The polymeric compositions are found to have elastic properties that are useful and desirable for inclusion in a variety of products. In particular, in one embodiment, the polymeric compositions exhibit a tension set from 200% elongation of less than 150% measured at 23° C. For example, if a film of the polymeric composition having a longitudinal dimension of 1 inch (2.54 cm) is stretched to elongate the film by 200%, i.e., to a length of 3 inches (7.62 cm), upon release, the film of the polymeric composition will return to a length that represents less than 150% elongation of the original length (2.5 inches/6.35 cm).

In addition to positive performance characteristics, the polymeric compositions exhibit beneficial processability characteristics as well. The unique combination of processability and performance attributes result in the polymeric compositions useful in a variety of applications such as films, fibers, woven and non-woven fabrics, sheets, molded objects, extruded forms, thermoformed objects, and all products made from such application materials.

The polymeric compositions comprise at least two polymeric components including a polymer having propylene-derived units and a styrenic block copolymer. The polymer having propylene-derived units is an elastomer having limited crystallinity resulting from a controlled disruption in isotactic propylene sequences of the polymer. The styrenic block copolymer component may be selected from any known styrenic block copolymers such as linear, radial, and star branched styrenic block copolymers.

The polymer having propylene-derived units and styrenic block copolymer may be combined by any suitable methods including melt-blending. The polymer having propylene-derived units and styrenic block copolymer may also be crosslinked though a variety of processes known in the art such as dynamic vulcanization or static vulcanization of shaped articles.

DETAILED DISCLOSURE

This disclosure relates to polymeric compositions that have processability characteristics enabling the compositions to be used in a variety of product forms while having beneficial physical properties such as elastic properties. For example, in one embodiment, the polymeric compositions demonstrate good processability in traditional processes like extrusion, injection molding, blow molding, compression molding, rotational molding, calendaring, etc., while exhibiting softness, good tensile strength, and low tension set and hysteresis. The combination of processability and physical properties makes the polymeric compositions useful in a variety of applications such as films, fibers, woven and non-woven fabrics, sheets, molded objects, extruded forms, thermoformed objects, and all products made from such application materials.

Elastomeric polymeric compositions are utilized in a wide variety of applications for which non-elastic polymeric compositions are unsuited. Exemplary of such applications are films, fibers, fabrics, extruded articles such as grips, injection-molded articles, etc. Elastomeric polymeric compositions are also used to produce fabrics for clothing in which a degree of freedom of movement is required. The elastomeric fabric structures must have enough unload stress to hold the garment in place when in use while having a low permanent set so that the garment will return generally to its original size and shape as the garment is worn and stretched over time.

The stress on unloading is an important elastic tensile property in most elastic applications. The unload stress of elastomeric articles provides an indication of the retractive force that holds the elastomeric article in place. In all elastomeric materials, the unload stress is lower than the load stress, i.e., the force required to extend the elastic article or material. The difference between the two is known as hysteresis, meaning that the force to extend is different that the force to hold in place.

Permanent set refers to the change between the length of an elastomeric material before and after its extension to a certain length for a certain time for a certain number of cycles. For example, the permanent set is the percent change in length of an elastic material after extension of the material to 100% or 200% of its initial length.

Typical elastic materials utilized in elastic applications include polyurethanes, ethylene-propylene rubbers ("EP" and "EPR"), including ethylene-propylene-diene terpolymers ("EPDM"), and styrenic block copolymers ('SBC's"). Polyurethanes have desirable unload stresses, permanent set and repeatability of use in many applications. However, polyurethanes have relatively high specific gravities resulting in lower yields of polyurethane articles for a given weight of material, leading to higher costs to produce such articles. Moreover, in the case of certain applications, such as disposable garments and diapers, polyurethanes are expensive for such one-time use applications.

For many applications, such as for garments, EP's and EPDM's have poor intrinsic physical properties and generally these materials must be blended with a plastic material such as a low density polyethylene, linear low density polyethylene, or ethylene vinyl acetate copolymers.

Elastomeric SBC's suffer from the disadvantage that they cannot be drawn to desired thicknesses and must be blended with other materials such as ethylene vinyl acetate copolymers, ethylene methacrylate copolymers, or low density polyethylene plastomers to achieve beneficial processability characteristics.

Moreover, conventional elastic materials typically must be melt welded to bond to a polyolefin substrate such as a polyolefin layer of a garment.

The polymeric compositions described herein are capable of providing a different and generally improved balance of properties compared to other polymeric compositions.

Many thermoplastic elastomer compositions exhibit a trade-off between processability and physical properties. For example, elastomers with beneficial physical properties such as EP's, SBC's, and polyurethanes are difficult to process into useful articles. Among these elastomers, increases in hardness, flexural modulus, and tensile strength are typically accompanied by losses in elastic properties, such as elastic recovery and hysteresis. The polymeric compositions described herein exhibit beneficial processability characteristics.

It has been discovered that certain polymer materials incorporating propylene-derived units blended with SBC's provide polymeric compositions with an improved balance among the following properties:

A) Processability—the ease with which a rubbery material, usually difficult to extrude, can be extruded at high line speeds. This influences the draw-down into films from an extrusion die and is assisted by a desired level of melt elasticity;
B) Elasticity—high elastic extension and recovery, even after many cycles. Related to this is the set, that is to say, the extent to which an elastically deformed object returns to its original shape and the number of deformations that can be accommodated without significant permanent deformation. The set can be measured in extension or compression.
C) Softness—the minimum force needed to have an elastic material conform in shape to another object in contact with it. This is normally reflected in a hardness parameter; in this case Shore A hardness.
D) Tensile strength or tear resistance—the force that can be applied to an elastic material in an elastically extended condition. Tensile strength is closely related to the tear strength.
E) Service temperature—the retention of the mechanical properties at different temperatures. At the upper end, this can be reflected in the softening point of the material such as a Vicat softening point. At the lower end, the glass transition temperature determines the point at which a polymer matrix becomes brittle.

More specifically, in certain embodiments, the polymeric compositions provide additional control of processability, softness and service temperature without significantly detracting from underlying tensile and permanent set characteristics.

In one embodiment, the polymeric compositions include at least two components. The first component is a polymer including propylene-derived units having a heat of fusion of less than 75 J/g with the polymer having an isotactic triad fraction of about 65% to about 99% and the second component is a styrenic block copolymer. In one embodiment, the first component may represent from about 1 wt. % to about 99 wt. % of the polymeric compositions and the second component may represent from about 1 wt. % to about 99 wt. % of the polymeric compositions while the compositions exhibit a tension set from 200% elongation of less than 150% at 23° C. In another embodiment, the polymeric compositions exhibit a tension set from 200% elongation of less than 100% at 23° C. In a third embodiment, the polymeric compositions exhibit a tension set from 200% elongation of less than 75% at 23° C. In still another embodiment, the polymeric compositions exhibit a tension set from 200% elongation of less than 50% at 23° C. In another embodiment, the polymeric compositions exhibit a tension set from 200% elongation of less than 25% at 23° C. In another embodiment, the polymeric compositions exhibit a tension set from 100% elongation of less than 75% at 23° C. In yet another embodiment, the polymeric compositions exhibit a tension set from 100% elongation of less than 50% at 23° C. In yet another embodiment, the polymeric compositions exhibit a tension set from 100% elongation of less than 25% at 23° C.

In one embodiment, the combined weights of the polymer including propylene-derived units and the styrenic block copolymer comprise from about 50 wt. % to about 100 wt. % of the polymeric composition. In another embodiment, the combined weights of the first component polymer including propylene-derived units and second component styrenic block copolymer comprise from about 50 wt. % to about 90 wt. % of the polymeric composition. In still another embodiment, the combined weights of the polymer including propylene-derived units and the styrenic block copolymer comprise from about 60 wt % to about 80 wt. % of the polymeric composition.

In one embodiment, the polymeric compositions described herein have a Shore A hardness of less than 90. In another embodiment, the polymeric compositions described herein have a Shore A hardness of less than about 80. In still another embodiment, the polymeric compositions described herein have a Shore A hardness of about 25 to about 80.

In one embodiment, the polymeric compositions have an MFR of about 0.1 to about 100. In another embodiment, the polymeric compositions have an MFR of about 1 to about 40.

In still another embodiment, the polymeric compositions have an MFR of about 2 to about 20.

In embodiment, the polymeric compositions have a tensile strength of at least 4 MPa. In another embodiment, the polymeric compositions have a tensile strength of less than about 40 MPa. In still another embodiment, the polymeric compositions have a tensile strength of at least 6 MPa.

In one embodiment, the polymeric compositions have a Vicat softening point of at least 40° C. In another embodiment, the polymeric compositions have a Vicat softening point of at least 50° C. In a third embodiment, the polymeric compositions have a Vicat softening point of at least 60° C. In still another embodiment, the polymeric compositions have a Vicat softening point of about 40° C. to about 60° C. In other embodiments, the polymeric compositions have Vicat softening points not exceeding 120° C.

In one embodiment, the polymer having propylene-derived units has isotactic triad fractions of about 65% to about 99%. In another embodiment, the polymer having propylene-derived units has isotactic triad fractions of about 70% to about 98%. In still another embodiment, the polymer having propylene-derived units has isotactic triad fractions of about 75% to about 97%.

In one embodiment, the styrenic block copolymer of the polymeric compositions has styrene contents of about 5 wt. % to about 95 wt. %. In another embodiment, the styrenic block copolymers of the polymeric compositions have styrene contents of about 10 wt. % to about 85 wt. %. In still other embodiments, the styrenic block copolymers of the polymeric compositions have styrene contents of about 15 wt. % to about 70 wt. %.

In one embodiment, the polymeric compositions have an MFR of about 0.1 to about 100, a Shore A hardness of less than 90, a tensile strength of at least 2 MPa, a Vicat softening point of at least 40° C., with the polymer component comprising propylene-derived units having an isotactic triad fraction of about 65% to about 99%, and the styrenic block copolymer having a styrene content of about 5 wt. % to about 95 wt. %.

In other embodiments, the polymeric compositions may include a variety of other polymeric components and additives. The various components of the polymeric compositions may be combined by any suitable method such as blending, including melt blending. Additionally, two or more of the polymeric components of the compositions may be crosslinked.

The various components of the polymeric composition are described as follows.

Polymer Component Including Propylene-Derived Units (PPU)

The first component polymer including propylene-derived units ("PPU") has crystalline regions interrupted by non-crystalline regions. The non-crystalline regions may result from regions of non-crystallizable polypropylene segments and/or the inclusion of comonomer units. The crystallinity and the melting point of the PPU are reduced compared to highly isotactic polypropylene by the introduction of errors in the insertion of propylene and/or by the presence of comonomer.

In one embodiment, the PPU comprises at least 75 wt. % of propylene-derived units. In another embodiment, the PPU comprises from 75 wt. % to 95 wt. % of propylene-derived units. In still another embodiment, the PPU comprises from 80 wt. % to 90 wt. % of propylene-derived units.

In one embodiment, the PPU has a Shore A hardness of less than about 90. In another embodiment, the PPU a Shore A hardness of about 45 to about 90. In still another embodiment, the PPU has a Shore A hardness of about 55 to about 80.

In one embodiment, the PPU has an MFR of about 0.5 to about 200. In another embodiment, the PPU has an MFR of about 1 to about 100. In still another embodiment, the PPU has an MFR of about 1 to about 50.

The crystallinity of the PPU may be expressed in terms of heat of fusion. In certain embodiments, the PPU has a heat of fusion, as determined by DSC, ranging from a lower limit of 1.0 J/g, or 1.5 J/g, or 3.0 J/g, or 4.0 J/g, or 6.0 J/g, or 7.0 J/g, to an upper limit of 30 J/g, or 40 J/g, or 50 J/g, or 60 J/g, or 75 J/g. Without being bound by theory, it is believed that the PPU described herein has generally isotactic crystallizable propylene sequences, and the heats of fusion described above are thought to result from melting of these crystalline segments. In one embodiment, the PPU has a heat of fusion of less than 60 J/g. In one embodiment, the level of crystallinity of the PPU is also reflected in a lower melting point.

In one embodiment, the PPU has a weight average molecular weight ($M_w$) within the range having an upper limit of 5,000,000 g/mol, or 1,000,000 g/mol, or 500,000 g/mol, and a lower limit of 10,000 g/mol, or 15,000 g/mol, or 20,000 g/mol, or 80,000 g/mol, and a molecular weight distribution $M_w/M_n$ (MWD), sometimes referred to as a "polydispersity index" (PDI), within the range having an upper limit of 40, or 20, or 10, or 5, or 4.5, and a lower limit of 1.5, or 1.8, or 2.0.

In one embodiment, the PPU has an isotactic triad fraction of about 65% to about 99%. In another embodiment, the PPU has an isotactic triad fraction of about 70% to about 98%. In still another embodiment, the PPU has an isotactic triad fraction of about 75% to about 97%. The isotactic triad fraction of a polymer is the relative tacticity of a sequence of three adjacent propylene units, a chain consisting of head to tail bonds, expressed as a binary combination of m and r sequences. It is usually expressed for PPUs of the present invention as the ratio of the number of units of the specified tacticity to all of the propylene triads in the copolymer. The triad fraction (mm fraction) of a propylene copolymer can be determined from a $^{13}C$ NMR spectrum of the propylene copolymer and the following formula:

$$mm \text{ Fraction} = \frac{PPP(mm)}{PPP(mm) + PPP(mr) + PPP(rr)}$$

where PPP(mm), PPP(mr) and PPP(rr) denote peak areas derived from the methyl groups of the second units in the following three propylene unit chains consisting of head-to-tail bonds:

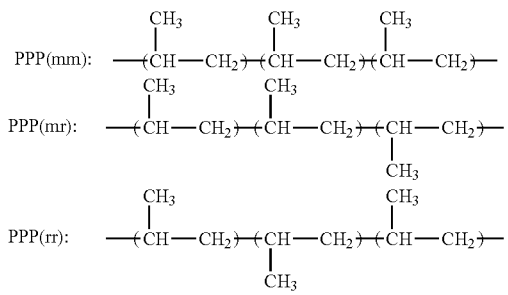

The $^{13}C$ NMR spectrum of the propylene copolymer is measured as described in U.S. Pat. No. 5,504,172. The spectrum relating to the methyl carbon region (19-23 parts per million (ppm)) can be divided into a first region (21.2-21.9 ppm), a second region (20.3-21.0 ppm) and a third region (19.5-20.3 ppm). Each peak in the spectrum was assigned with reference to, an article in the journal Polymer, Volume 30 (1989), page 1350. In the first region, the methyl group of the second unit in the three propylene unit chain represented by PPP (mm) resonates. In the second region, the methyl group of the second unit in the three propylene unit chain represented by PPP (mr) resonates, and the methyl group (PPE-methyl group) of a propylene unit whose adjacent units are a propylene unit and an ethylene unit resonates (in the vicinity of 20.7 ppm). In the third region, the methyl group of the second unit in the three propylene unit chain represented by PPP (rr) resonates, and the methyl group (EPE-methyl group) of a propylene unit whose adjacent units are ethylene units resonates (in the vicinity of 19.8 ppm). The calculation of the triad fraction is outlined in the techniques shown in U.S. Pat. No. 5,504,172. Subtraction of the peak areas for the error in propylene insertions (both 2.1 and 1.3) from peak areas from the total peak areas of the second region and the third region, the peak areas based on the 3 propylene units-chains (PPP (mr) and PPP(rr)) consisting of head-to-tail bonds can be obtained. Thus, the peak areas of PPP(mm), PPP(mr) and PPP(rr) can be evaluated, and hence the triad tacticity of the propylene unit chain consisting of head-to-tail bonds can be determined.

In some embodiments, the crystallinity of the PPU is reduced by the copolymerization of propylene with limited amounts of one or more comonomers selected from: ethylene, $C_4$-$C_{20}$ alpha-olefins, and polyenes. In one embodiment, the PPU comprises at least 5 wt. % of the alpha-olefin comonomer units. In another embodiment, the PPU comprises about 10 wt. % to about 20 wt. % of the alpha-olefin comonomer units. In another embodiment, the PPU comprises from about 75 wt. % to about 95 wt. % propylene-derived units and from about 5 wt. % to about 25 wt. % of the ethylene-derived units. In still another embodiment, the PPU comprises from about 80 wt. % to about 95 wt. % propylene-derived units and from about 5 wt. % to about 20 wt. % the ethylene-derived units. In an additional embodiment, the PPU comprises at least 70 wt. % of propylene-derived units and about 5.0 wt. % to about 30.0 wt. % of ethylene-derived units.

The optional polyene units may be derived from any hydrocarbon structure having at least two unsaturated bonds wherein at least one of the unsaturated bonds may be incorporated into a polymer. For example, the optional polyene may be selected from straight chain acyclic olefins, such as 1,4-hexadiene and 1,6-octadiene; branched chain acyclic olefins, such as 5-methyl-1,4-hexadiene, 3,7-dimethyl-1,6-octadiene, and 3,7-dimethyl-1,7-octadiene; single ring alicyclic olefins, such as 1,4-cyclohexadiene, 1,5-cyclooctadiene, and 1,7-cyclododecadiene; multi-ring alicyclic fused and bridged ring olefins, such as tetrahydroindene, norbornadiene, methyl-tetrahydroindene, dicyclopentadiene, bicyclo-(2.2.1)-hepta-2,5-diene, alkenyl norbornenes, alkylidene norbornenes, cycloalkenyl norbornenes, and cylcoalkyliene norbornenes (such as 5-methylene-2-norbornene, 5-ethylidene-2-norbornene, 5-propenyl-2-norbornene, 5-isopropylidene-2-norbornene, 5-(4-cyclopentenyl)-2-norbornene, 5-cyclohexylidene-2-norbornene, and 5-vinyl-2-norbornene); and cycloalkenyl-substituted alkenes, such as vinyl cyclohexene, allyl cyclohexene, vinyl cyclooctene, 4-vinyl cyclohexene, allyl cyclodecene, vinyl cyclododecene, divinyl benzene, and tetracyclo (A-11,12)-5,8-dodecene.

In one embodiment, the PPU incorporates from about 1 wt. % to about 12 wt. % of polyene-derived units, based on the combined weight of the propylene-derived units and the alpha-olefin-derived units, if any. In another embodiment, the PPU incorporates from about 1.0 wt. % to about 9.0 wt. % of polyene-derived units, based on the combined weight of the propylene-derived units and the alpha-olefin-derived units, if any. In another embodiment, the PPU incorporates from about 2.0 wt. % to about 7.0 wt. % of polyene-derived units, based on the combined weight of the propylene-derived units and the alpha-olefin-derived units, if any. In yet another embodiment, the PPU incorporates from about 3.0 wt. % to about 5.0 wt. % of polyene-derived units, based on the combined weight of the propylene-derived units and the alpha-olefin-derived units, if any.

In one embodiment, the polyene-derived units are derived from 5-ethylidene-2-norbornene. In another embodiment, the polyene-derived units are derived from 5-vinyl-2-norbornene. In still another embodiment, the polyene-derived units are derived from divinyl benzene.

The polymeric compositions described herein are not limited by any particular polymerization method for preparing the PPU of the invention, and the polymerization processes described herein are not limited by any particular type of reaction vessel.

In one embodiment, the catalyst system used to produce the PPU includes one or more transition metal compounds and one or more activators. When alumoxane or aluminum alkyl activators are used, the combined pre-catalyst-to-activator molar ratio is from 1:5000 to 10:1. When ionizing activators are used, the combined pre-catalyst-to-activator molar ratio is from 10:1 to 1:10. Multiple activators may be used, including using mixtures of alumoxanes or aluminum alkyls with ionizing activators. In other embodiments, the methods and catalyst systems disclosed in U.S. Patent Application 20040024146 published Feb. 5, 2004 may be used to produce the PPU. In still other embodiments, the PPU may be produced using catalyst systems such as the nonmetallocene, metal-centered, heteroaryl ligand catalyst systems as described in U.S. Patent Application 20030204017 published Oct. 30, 2003.

One or more reactors in series or in parallel may be used in the present invention. The catalyst component and activator may be delivered as a solution or slurry, either separately to the reactor, activated in-line just prior to the reactor, or preactivated and pumped as an activated solution or slurry to the reactor. Polymerizations are carried out in either single reactor operation, in which monomer, comonomers, catalyst/activator, scavenger, and optional modifiers are added continuously to a single reactor or in series reactor operation, in which the above components are added to each of two or more reactors connected in series. The catalyst components can be added either to the first reactor in the series or to both reactors with one component being added to first reaction and another component to the other reactors.

Exemplary PPU's are commercially available from ExxonMobil Chemical under the tradename Vistamaxx™ and from The Dow Chemical Company under the tradename Versify™.

For further general process condition information suitable for use in preparing the PPU's, see U.S. Pat. No. 5,001,205 and PCT publications WO 96/33227 and WO 97/22639. For further information on gas phase polymerization processes, see U.S. Pat. Nos. 4,543,399; 4,588,790; 5,028,670; 5,317,036; 5,352,749; 5,405,922; 5,436,304; 5,453,471; 5,462,999; 5,616,661; 5,627,242; 5,665,818; 5,668,228; and 5,677,375, and European publications EP-A-0 794 200; EP-A-0 802 202; and EP-B-634 421. For information relating to methods of introducing liquid catalyst systems into fluidized bed polymerizations into a particle lean zone, see U.S. Pat. No. 5,693,727. For further information on slurry polymerization processes, see U.S. Pat. Nos. 3,248,179 and 4,613,484. PCT publication WO 96/08520 and U.S. Pat. No. 5,712,352 describe a polymerization process operated in the absence of or essentially free of any scavengers, although the use of scavengers is contemplated for producing the PPU described herein.

In one embodiment, the polymeric compositions described herein incorporate from about 1 wt. % to about 99 wt. % of the PPU first component. In another embodiment, the polymeric compositions described herein incorporate from about 5 wt. % to about 95 wt. % of the PPU first component. In a second embodiment, the polymeric compositions described herein incorporate from about 10 wt. % to about 90 wt. % of the PPU first component. In a third embodiment, the polymeric compositions described herein incorporate from about 20 wt. % to about 80 wt. % of the PPU first component. In other embodiments, the polymeric compositions described herein incorporate from about 40 wt. % to about 60 wt. % of the PPU first component. Any upper limit recited may, of course, be combined with any lower limit for selected sub-ranges.

Styrenic Block Copolymer (SBC)

A wide variety of styrenic block copolymers ("SBC") are useful as the second component for preparing the polymeric compositions described herein. Linear block copolymers, A-B diblock copolymers, A-B-A triblock copolymers, A-B-A-B tetrablock copolymers, A-B-A-B-A pentablock copolymers, and the like.

Such SBC's generally comprise a thermoplastic block portion A and an elastomeric block portion B. The block copolymers suitable for use herein are thermoplastic and elastomeric. The SBC's are elastomeric in the sense that they generally form a three-dimensional physical crosslinked or entangled structure below the glass transition temperature ($T_g$) of the thermoplastic block portion such that they exhibit elastic memories in response to external forces. The SBC's are thermoplastic in the sense that they can be melted above the endblock $T_g$, formed, and resolidified several times with little or no change in physical properties, assuming minimum oxidative degradation.

The block portion A are the hard blocks and are derived from materials which have a sufficiently high glass transition temperature to form crystalline or glassy domains at the use temperature of the polymer. Such hard blocks generally form strong physical "crosslinks" or agglomerates with other hard blocks in the copolymers. The hard block portion, A, generally comprises a polyvinylarene derived from monomers such as styrene, alpha-methyl styrene, other styrene derivatives, or mixtures thereof. The hard block portion A may also be a copolymer derived from styrenic monomers such as those described above and olefinic monomers such as ethylenes, propylenes, butylenes, isoprenes, butadienes, and mixtures thereof.

In one embodiment, the hard block portion A is polystyrene, having a number-average molecular weight between from about 1,000 to about 200,000, preferably from about 2,000 to about 100,000, more preferably from about 5,000 to about 60,000. Typically the hard block portion A comprises from about 5% to about 80%, preferably from about 10% to about 70%, more preferably from about 10 to about 50% of the total weight of the copolymer.

The material forming the B-block will have sufficiently low glass transition temperature at the use temperature of the polymer such that crystalline or glassy domains are not formed at these working temperatures. The B-block may thus be regarded as a soft block. The soft block portion B is typically an olefinic polymer derived from conjugated aliphatic diene monomers of from about 4 to about 6 carbon atoms or linear alkene monomers of from about 2 to about 6 carbon atoms. Suitable diene monomers include butadiene, isoprene, and the like. Suitable alkene monomers include ethylene, propylene, butylene, and the like. The soft block portion B preferably comprises a substantially amorphous polyolefin such as ethylene/propylene polymers, ethylene/butylene polymers, polyisoprene, polybutadiene, and the like or mixtures thereof. The number-average molecular weight of the soft block B is typically from about 1,000 to about 300,000, preferably from about 10,000 to about 200,000, and more preferably from about 20,000 to about 100,000. Typically the soft block portion B comprises from about 20% to about 90%, preferably from about 30% to about 80%, more preferably from about 40% to about 80% of the total weight of the copolymer.

Suitable SBC's for use in the polymeric compositions described herein include at least one substantially thermoplastic block portion A and at least one substantially elastomeric block portion B. The SBC's may have multiple blocks.

In one embodiment, the SBC's may be an A-B diblock copolymer. In another embodiment, the block copolymer may be an A-B-A triblock copolymer. In other embodiments, the SBC's may be selected as A-B-A-B tetrablock copolymers, or A-B-A-B-A pentablock copolymers.

In embodiment, the SBC's are triblock copolymers having an elastomeric midblock B and thermoplastic endblocks A and A', wherein A and A' may be derived from different vinylarene monomers. In other embodiments, the SBC's have more than one A block and/or more than one B block, wherein each A block may be derived from the same or different vinylarene monomers and each B block may be derived from the same or different olefinic monomers.

The SBC's may also be radial, having three or more arms, each arm being an B-A, B-A-B-A, or the like type copolymer and the B blocks being at or near the center portion of the radial polymer. In other embodiments, the SBC's may have four, five, or six arms.

In one embodiment, the olefin block comprises at least about 50 wt. % of the block copolymer. The unsaturation in olefinic double bonds may be selectively hydrogenated to reduce sensitivity to oxidative degradation and may have beneficial effects on the elastomeric properties. For example, a polyisoprene block can be selectively reduced to form an ethylene-propylene block. In one embodiment, the vinylarene block typically comprises at least about 10 percent by weight of the SBC. However, higher vinylarene contents may be selected for high elastic and low stress relaxation properties.

Exemplary suitable SBC's for use in for inclusion in the polymeric compositions described herein are styrene-olefin-styrene triblock copolymers such as styrene-butadiene-styrene (S-B-S), styrene-ethylene/butylene-styrene (S-EB-S), styrene-ethylene/propylene-styrene (S-EP-S), styrene-isoprene-styrene (S-I-S), and mixtures thereof. The SBC may be a selected SBC or a blend of SBC's.

The SBC's may also be used in the polymeric compositions described herein as a blend of one or more SBC's blended with one or more other substantially less elastomeric polymers such as polypropylene, polyethylene, polybutadiene, polyisoprene, or mixtures thereof.

In one embodiment, the SBC's for use in the polymeric compositions described herein are polystyrene-ethylene/butylene-polystyrene block copolymers having a styrene content in excess of about 10 weight percent. With higher styrene content, the polystyrene block portions generally have a relatively high molecular weight.

In one embodiment, the SBC has a melt flow rate of about 0.01 to about 150. In another embodiment, the SBC has a melt flow rate of about 0.1 to about 100. In still another embodiment, the SBC has a melt flow rate of about 1 to about 75.

In one embodiment, the polymeric composition includes a SBC comprised of triblock segments comprised of styrene-derived units and at least one other unit selected from the group consisting of ethylene-derived units, butadiene-derived units, isoprene-derived units, isobutylene-derived units and wherein the styrenic block copolymer is comprised of less than 20 wt. % of diblock segments. In another embodiment, the polymeric composition incorporates a SBC comprised of segments selected from the group consisting of SIS, SBS, SEBS, SEPS, and SIBS units and wherein from about 5% to about 95% of diene units in the styrenic block copolymer are hydrogenated.

Exemplary SBC's for use in the polymeric compositions described herein are commercially available from Dexco Polymers LP under the designation Vector™ and under the designation Kraton® from Kraton Polymers.

In one embodiment, the polymeric compositions described herein incorporate from about 1 wt. % to about 99 wt. % of the SBC second component. In another embodiment, the polymeric compositions described herein incorporate from about 5 wt. % to about 95 wt. % of the SBC second component. In a second embodiment, the polymeric compositions described herein incorporate from about 10 wt. % to about 90 wt. % of the SBC second component. Any upper limit recited may, of course, be combined with any lower limit for selected subranges.

Additional Components

As mentioned above, the polymeric compositions described herein may include polymeric and additive components in addition to the PPU and SBC components described above. The following is a description of exemplary additional components.

Third Polymer Component (TPC)

In some embodiments, the polymeric compositions described herein may include a second polymer incorporating propylene-derived units that will be referred to as a third polymer component ("TPC"). The TPC, which in some embodiments may have isotactic propylene-type crystallinity, may be selected from: propylene homopolymers, propylene copolymers, and mixtures thereof, including mixtures of the type commonly referred to as reactor copolymers or impact copolymers. In embodiments where the TPC includes a propylene copolymer, the propylene copolymer may be a graft copolymer, block copolymer, reactor made polypropylene ethylene-propylene copolymer blend, or random copolymer.

In some embodiments, the amount of propylene-derived units present in the TPC is 90 wt. % or higher, or 92 wt. % or higher, or 95 wt. % or higher, or 97 wt. % or higher, or 100 wt. %, based on the total weight of the TPC. If the TPC is a reactor polypropylene ethylene-propylene copolymer blend, the total amount of ethylene in the copolymer blend is within the range of 1 wt. % to 40 wt. %. In one embodiment, the TPC has an isotactic triad fraction of about 50% to about 99%. In another embodiment, the TPC has an isotactic triad fraction of about 70% to about 98%. In still another embodiment, the TPC has an isotactic triad fraction of about 80% to about 98%.

In one embodiment, the TPC includes a random copolymer of propylene and at least one comonomer selected from one or more of: ethylene and $C_4$-$C_{12}$ alpha-olefins. In certain embodiments, the amount of comonomer is within the range having an upper limit of 15 wt. %, or 13 wt. %, or 11 wt. %, or 9 wt. %, or 8 wt. %, or 6 wt. %, and a lower limit of 2 wt. %, based on the total weight of the TPC. In one embodiment, the TPC incorporates from about 2 wt. % to about 10 wt. % of the comonomer units.

In certain embodiments, the TPC has a melting point by DSC of at least 80° C., or at least 100° C., or at least 110° C., or at least 115° C., or at least 130° C. and a heat of fusion, as determined by DSC, of at least 40 J/g, or at least 50 J/g, or at least 60 J/g, or at least 70 J/g, or at least 80 J/g.

In various embodiments, the TPC has a weight average molecular weight ($M_w$) within the range having an upper limit of 5,000,000 g/mol, or 500,000 g/mol, and a lower limit of 10,000 g/mol, or 50,000 g/mol, and a molecular weight distribution $M_w/M_n$ (MWD), sometimes referred to as a "polydispersity index" (PDI), within the range having an upper limit of 40 and a lower limit of 1.5.

The TPC may be prepared by any of various methods. In one embodiment, the TPC may be a propylene homopolymer obtained by a well known process for the homopolymerization of propylene in a single stage or multiple stage reactor. In another embodiment, the TPC may be a propylene copolymer obtained by a well known process for copolymerizing propylene and one or more comonomers in a single stage or multiple stage reactor.

Polymerization methods for preparing the TPC include high pressure, slurry, gas, bulk, solution phase, and combinations thereof. Catalyst systems that can be used include traditional Ziegler-Natta catalysts and single-site metallocene catalyst systems. In one embodiment, the catalyst used has a high isospecificity.

Polymerization of the TPC may be carried out by a continuous or batch process and may include the use of chain transfer agents, scavengers, or other such additives well known to those skilled in the art. The TPC may also contain additives such as flow improvers, nucleators, and antioxidants which are normally added to isotactic polypropylene to improve or retain properties.

In one embodiment, the polymeric compositions described herein incorporate from about 1 wt. % to about 70 wt. % of the TPC. In another embodiment, the polymeric compositions described herein incorporate from about 5 wt. % to about 60 wt. % of the TPC. In a second embodiment, the polymeric compositions described herein incorporate from about 10 wt. % to about 40 wt. % of the TPC. Any upper limit recited may, of course, be combined with any lower limit for selected sub-ranges.

Fourth Polymer Component (FPC)

Some embodiments of the polymeric compositions described herein include a polymer component ("FPC"). The FPC, which in some embodiments may have ethylene-type crystallinity, may be a copolymer of ethylene and a second alpha-olefin. In another embodiment, the FPC may be a polymer comprising monomer units selected from ethylene, another alpha-olefin, and a diene. In one embodiment, the level of ethylene-derived units in the FPC is 50 mol % or greater. In one embodiment, the FPC is an ethylene-octene copolymer. In another embodiment the FPC is a copolymer of ethylene, propylene, and diene, commonly referred to as "EPDM". In one embodiment, the level of propylene-derived units in the FPC is 40 mol % or greater.

In one embodiment, the polymeric compositions described herein incorporate from about 1 wt. % to about 70 wt. % of the FPC. In another embodiment, the polymeric compositions described herein incorporate from about 5 wt. % to about 60 wt. % of the FPC. In a third embodiment, the polymeric compositions described herein incorporate from about 10 wt. % to about 40 wt. % of the FPC. In another embodiment, the polymeric composition may incorporate from about 1 wt. % to about 35 wt. % of an ethylene copolymer having a density of about 0.85 to about 0.94. Any upper limit recited may, of course, be combined with any lower limit for selected subranges.

Crosslinked Polymer Components

In one embodiment, the elastomeric performance properties of the PPU may be improved by crosslinking the PPU, and/or the other polymeric components of the polymeric compositions described herein, to various degrees. In another embodiment, the PPU is crosslinked to various degrees to permit convenient processing. In some embodiments, as described above, the PPU may include a polyene to facilitate crosslinking and optimal end use performance in various options of formulation and processing. In other embodiments, such as when using radiation to induce the crosslinking reaction, the presence of diene in the PPU is optional.

The curing may be carried out to varying degrees. Initially, polymer chains may incorporated into other chains to form long chain branches. These polymers are more shear sensitive and easier to process. These properties may be accessed by determining the viscosity ratio under different shear conditions. For most applications, the polymer should remain capable of thermoplastic flow following curing. Curing may provide improved recovery from tensile deformation, improved stress relaxation, and prevent loss of shape of molded or extruded product and increase the service temperature for the article. The degree of crosslinking may vary and can be measured by determining the wt. % of insolubles in boiling xylene which, in one embodiment, may vary from about 10 wt. % to about 90 wt. %. Continued curing may lead to gelling and finally to the immobilization of the polymers from extensive crosslinking.

Curing may be effected by any suitable system capable of dehydrating the polymer chain, such as by using free radicals. In one embodiment, curing is accomplished through irradiation. Curing may also be effected chemically using functionalities in the polymer such as unreacted unsaturated end moieties that remain after diene incorporation. The crosslinking reaction may then be referred to as vulcanization. A crosslinking agent is used to activate the functionality such as sulfur based curatives, peroxide curatives, phenolic resin cure, hydrolilation, and labile or migratory cure systems such as sulfur dichloride.

Additives

The polymeric compositions describe herein may include one or more additive components in addition to the polymer components described above. Various additives may be present to enhance a specific property or may be present as a result of processing of the individual components. Additives which may be incorporated include, but are not limited to, fire retardants, antioxidants, plasticizers, pigments, vulcanizing or curative agents, vulcanizing or curative accelerators, cure retarders, processing aids, flame retardants, tackifying resins, flow improvers, and the like. Antiblocking agents, coloring agents, lubricants, mold release agents, nucleating agents, reinforcements, and fillers (including granular, fibrous, or powder-like) may also be employed. Nucleating agents and fillers may improve the rigidity of the article. The list described herein is not intended to be inclusive of all types of additives which may be employed with the present invention.

It will be appreciated that other additives may be employed to enhance properties of the composition. As is understood by those skilled in the art, the polymeric compositions may be modified to adjust the characteristics of the blend as desired.

In one embodiment, the polymeric compositions described herein incorporate about 1 wt. % to about 25 wt. % of a tackifier resin. In another embodiment, the polymeric compositions described herein incorporate about 2 wt. % to about 20 wt. % of a tackifier resin. In still another embodiment, the polymeric compositions described herein incorporate about 3 wt. % to about 15 wt. % of a tackifier resin.

The polymeric compositions described herein may also contain inorganic particulate fillers, which may improve the mechanical and wear properties of the compositions, particularly in compositions including crosslinked components. The amount of inorganic filler used is typically less than 60 wt. %, or less than 50 wt. %, or less than 40 wt. %, or less than 30 wt. %, based on the total weight of the composition. The inorganic fillers include particles less than 1 mm. in diameter, rods less than 1 cm in length, and plates less than 0.2 cm$^2$ in surface area. Exemplary particulate fillers include carbon black, clays, titanium and magnesium oxides, and silica. In addition, other particulate fillers, such as calcium carbonate, zinc oxide, whiting, and magnesium oxide, can also be used. An example of a rod-like filler is glass fiber. An exemplary plate-like filler is mica. The addition of very small particulates, commonly referred to as nanocomposites, is also contemplated. The addition of the fillers may change the properties of the compositions described herein. For example, polymeric compositions including inorganic filler may have improved thermal stability and resistance to wear. The addition of white fillers may improve the temperature changes of the hydrocarbon polymers on exposure to sunlight. The addition of fillers beyond a certain level may lead to a dramatic increase in the viscosity and a corresponding decrease in processability. This threshold level is referred to as the percolation threshold. In addition to the increase in viscosity, the percolation threshold is accompanied by an improvement in the elastic properties, and at levels slightly higher than the percolation threshold there is a drop in the elastic recovery of the blend. The percolation threshold is attained at different levels of addition of fillers depending on the type of filler used. Generally, the percolation threshold is attained at lower levels for fillers with a smaller size than for fillers with a larger size.

The compositions described herein may contain process oil in the range of from 0 to 500 parts by weight, or from 2 to 200 parts by weight, or from 5 to 150 parts by weight, or from 10 to 100 parts by weight, per hundred parts of total polymer. For purposes of this disclosure, the term "process oil" refers to any or a variety of oils having molecular weights (Mn) of less than 20,000. The addition of process oil in moderate amounts may lower the viscosity and flexibility of the blend while improving the properties of the blend at temperatures near and below 0° C. It is believed that these potential benefits arise by the lowering of the glass transition temperature (Tg) of the blend. Adding process oil to the blend may also improve processability and provide a better balance of elastic and tensile strength. The process oil is typically known as extender oil in rubber applications. Process oils include hydrocarbons having either (a) traces of hetero atoms such as oxygen or (b) at least one hetero atom such as dioctyl plithalate, ethers, and polyethers. Process oils have a boiling point to be substantially involatile at 200° C. These process oils are commonly available either as neat solids, liquids, or as physically absorbed mixtures of these materials on an inert support (e.g., clay, silica) to form a free flowing powder. Process oils usually include a mixture of a large number of chemical compounds which may consist of linear, acyclic but branched, cyclic, and aromatic carbonaceous structures. Another family of process oils is certain organic esters and alkyl ether esters having molecular weights (Mn) of less than 20,000. Combinations of process oils may also be used in the practice of the invention. The process oil should be compatible or miscible with the polymer blend composition in the melt, and may be substantially miscible in the PPU at room temperature. Process oils may be added to the blend compositions by any of the conventional means known in the art, including the addition of all or part of the process oil prior to recovery of the polymer, and addition of all or part of the process oil to the polymer as a part of a compounding for the interblending of the PPU. The compounding step may be carried out in a batch mixer, such as a mill, or an internal mixer, such as a Banbury mixer. The compounding operation may also be conducted in a continuous process, such as a twin screw extruder. The addition of process oils to lower the glass transition temperature of blends of isotactic polypropylene and ethylene propylene diene rubber is described in U.S. Pat. Nos. 5,290,886 and 5,397,832.

The addition of process aids, such as a mixture of fatty acid ester or calcium fatty acid soap bound on a mineral filler, to the compositions described herein may help the mixing of the composition and the injection of the composition into a mold. Other examples of process aids are low molecular weight polyethylene copolymer wax and paraffin wax. The amount of process aid used may be within the range of from 0.5 to 5 phr.

Adding antioxidants to the compositions described herein may improve the long term aging. Examples of antioxidants include, but are not limited to quinolein, e.g., trimethylhydroxyquinolein (TMQ); imidazole, e.g., zincmercapto toluoyl imidazole (ZMTI); and conventional antioxidants, such as hindered phenols, lactones, and phosphites. The amount of antioxidants used may be within the range of from 0.001 to 5 phr.

The polymeric compositions described herein may include one or more non-functionalized plasticizers ("NFP's") where the non-functionalized plasticizer has a kinematic viscosity ("KV") of 2 cSt or more at 100° C. For purposes of this disclosure, if the NFP has a flash point of less than 100° C. it is defined to have a KV at 100° C. of less than 2 cSt. In one embodiment, the non-functionalized plasticizer is polyalphaolefin oligomers of $C_5$ to $C_{14}$ olefins having a Kinematic viscosity of 10 cSt or more at 100° C. and a viscosity index of 120 or more. In one embodiment, the non-functionalized plasticizers incorporate oligomers of $C_5$ to $C_{14}$ olefins having a viscosity index of 120 or more. In another embodiment, the non-functionalized plasticizers include oligomers of $C_6$ to $C_{14}$ olefins having viscosity index of 120 or more. In still another embodiment, the non-functionalized plasticizers include linear and/or branched paraffinic hydrocarbon compositions produced by one or more gas to liquids process having a number average molecular weight of 500 to 20,000. For additional information regarding non-functionalized plasticizers, see PCT published application WO 04/014998.

In one embodiment, the polymeric compositions described herein incorporate from about 1 wt. % to about 95 wt. % of one or more non-functionalized plasticizers having a kinematic viscosity ("KV") of at least 2 cSt at 100° C. In another embodiment, the polymeric compositions described herein incorporate from about 5 wt. % to about 85 wt. % of one or more non-functionalized plasticizers having a kinematic viscosity ("KV") of at least 2 cSt at 100° C. In still another embodiment, the polymeric compositions described herein incorporate from about 5 wt. % to about 75 wt. % of one or more non-functionalized plasticizers having a kinematic viscosity ("KV") of at least 2 cSt at 100° C. In one embodiment, the flashpoint of the non-functionalized plasticizers is at least 200° C. In another embodiment, the flashpoint of the non-functionalized plasticizers is at least 195° C. In still another embodiment, the flashpoint of the non-functionalized plasticizers is at least 190° C.

In one embodiment, the polymeric compositions described herein include about 1 wt. % to about 60 wt. % of an additive selected from the group consisting of a filler, a pigment, a coloring agent, a processing oil, a plasticizer, and mixtures thereof. In another embodiment, the polymeric compositions described herein include about 5 wt. % to about 50 wt. % of an additive selected from the group consisting of a filler, a pigment, a coloring agent, a processing oil, a plasticizer, and mixtures thereof. In still another embodiment, the polymeric compositions described herein include about 10 wt. % to about 40 wt. % of an additive selected from the group consisting of a filler, a pigment, a coloring agent, a processing oil, a plasticizer, and mixtures thereof.

Blending Polymeric Components and Additives

The compositions described herein may be prepared by any procedure that provides an intimate mixture of the polymeric components. Generally, the first step of the process is mixing the polymeric components and optional additives, such as process oil, fillers, colorants, antioxidants, nucleators, and flow improvers using equipment such as, but not limited to a Carver press for melt pressing the components together, internal mixers such as a Banbury mixer or a Brabender mixer for solution or melt blending of the components, and equipment used for continuous mixing procedures including single and twin screw extruders, static mixers, impingement mixers, as well as other machines and processes designed to disperse the components in intimate contact. A complete mixture of the polymeric components is indicated by the uniformity of the morphology of the composition. Such procedures are well known.

In embodiments in which crosslinking of the polymeric components is desired, the next step is mixing a chemical curative, such as peroxides or sulfur compounds, with the intimate mixture, and then fabricating the intimate mixture including the chemical curative into the final shape of the article and raising the temperature for an extended period of time to allow the crosslinking to take place. In another embodiment, the next step is fabricating the intimate mixture into the final shape of the article, and then exposing the fabricated mixture to an external curative agent, such as high energy radiation, to allow crosslinking of the PPU.

For addition information regarding processes for preparation of polymeric blend compositions, including the crosslinking of polymeric components, see copending U.S. Patent Application Ser. No. 60/519,975 filed Nov. 14, 2003.

Processed Polymeric Compositions

As discussed above, the unique combination of processability and performance attributes of the polymeric compositions described herein make them useful to produce a variety of different types of materials to produce a wide assortment of products. Among the materials that may be produced using the polymeric compositions described herein are films, fibers, woven and non-woven fabrics, sheets, molded objects, extruded forms, and thermoformed objects. The following describes the manner in which some of these materials may be formed from the polymeric compositions described herein.

Fibers

In one embodiment, the polymeric compositions may be used to produce fibers. Methods for making fibers from polymeric compositions are well known. Fibers of the invention may have desirable softness and elastic properties and may be used in various applications, for example, continuous filament yarn, bulked continuous filament yarn, staple fibers, melt blown fibers, and spunbound fibers. In a particular aspect of this embodiment, fibers comprising a composition described herein may have the following advantage—it may be easily spun into fibers by extrusion through a spinneret followed by drawing to the desired denier.

In one embodiment, the elastic recovery, stress relaxation, and tensile recovery properties of the fibers of the invention may be enhanced by annealing and/or mechanical orientation. Annealing partially relieves the internal stress in the stretched fiber and restores the elastic recovery properties of the blend in the fiber. Annealing has been shown to lead to significant changes in the internal organization of the crystalline structure and the relative ordering of the amorphous and semicrystalline phases, which leads to recovery of the elastic properties. The fiber may be annealed at a temperature of at least 4-5° C. above room temperature, or at least 6-7° C. above room temperature, but slightly below the crystalline melting point of the blend composition. Thermal annealing is conducted by maintaining the polymer fiber at a temperature of from room temperature to 160° C., or 130° C., for a period of from 15 seconds to 7 days. A typical annealing period is 3 days at 50° C. or 5 minutes at 100° C. The annealing time and temperature can be adjusted for any particular polymer fiber by experimentation. It is believed that during this annealing process, there is intermolecular rearrangement of the polymer chains, leading to a material with greater recovery from tensile deformation than the unannealed material. Annealing of the fiber is done in the absence of mechanical orientation; however, mechanical orientation can be a part of the annealing process, e.g., after the extrusion operation.

Mechanical orientation can be done by the temporary, forced extension of the polymer fiber for a short period of time before it is allowed to relax in the absence of extensional forces. It is believed that the mechanical orientation of the fiber leads to reorientation of the crystallizable portions of the fiber. Oriented polymer fibers are conducted by maintaining the polymer fibers at an extension of 100% to 700% for a period of 0.1 seconds to 24 hours. A typical orientation is an extension of 200% for a momentary period at room temperature.

For orientation of a fiber, the polymeric fiber at an elevated temperature, but below the crystalline melting point of the polymer, is passed from a feed roll of fiber around two rollers driven at different surface speeds and finally to a take-up roller. The driven roller closest to the take-up roll is driven faster than the driven roller closest to the feed roll, such that the fiber is stretched between the driven rollers. The assembly may include a roller intermediate the second roller and take-up roller to cool the fiber. The second roller and the take-up roller may be driven at the same peripheral speeds to maintain the fiber in the stretched condition. If supplementary cooling is not used, the fiber will cool to ambient temperature on the take-up roller.

In one embodiment, the invention provides fabrics made with the fibers of the invention. The fabrics may be made by any of the known processes for making non-woven or woven fabrics.

Molded Products

The plasticized polyolefin composition described above may also be used to prepare molded products in any molding process, including but not limited to, injection molding, gas-assisted injection molding, extrusion blow molding, injection blow molding, injection stretch blow molding, compression molding, rotational molding, foam molding, thermoforming, sheet extrusion, and profile extrusion. The molding processes are well known to those of ordinary skill in the art.

The compositions described herein may be shaped into desirable end use articles by any suitable means known in the art. Thermoforming, vacuum forming, blow molding, rotational molding, slush molding, transfer molding, wet lay-up or contact molding, cast molding, cold forming matched-die molding, injection molding, spray techniques, profile co-extrusion, or combinations thereof are typically used methods.

Thermoforming is a process of forming at least one pliable plastic sheet into a desired shape. An embodiment of a thermoforming sequence is described, however this should not be construed as limiting the thermoforming methods useful with the compositions of this invention. First, an extrudate film of the composition of this invention (and any other layers or materials) is placed on a shuttle rack to hold it during heating. The shuttle rack indexes into the oven which pre-heats the film before forming. Once the film is heated, the shuttle rack indexes back to the forming tool. The film is then vacuumed onto the forming tool to hold it in place and the forming tool is closed. The forming tool can be either "male" or "female" type tools. The tool stays closed to cool the film and the tool is then opened. The shaped laminate is then removed from the tool.

Thermoforming is accomplished by vacuum, positive air pressure, plug-assisted vacuum forming, or combinations and variations of these, once the sheet of material reaches thermoforming temperatures, typically of from 140° C. to 185° C. or higher. A pre-stretched bubble step is used, especially on large parts, to improve material distribution. In one embodiment, an articulating rack lifts the heated laminate towards a male forming tool, assisted by the application of a vacuum from orifices in the male forming tool. Once the laminate is firmly formed about the male forming tool, the thermoformed shaped laminate is then cooled, typically by blowers. Plug-assisted forming is generally used for small, deep drawn parts. Plug material, design, and timing can be critical to optimization of the process. Plugs made from insulating foam avoid premature quenching of the plastic. The plug shape is usually similar to the mold cavity, but smaller and without part detail. A round plug bottom will usually promote even material distribution and uniform side-wall thickness. For a semicrystalline polymer such as polypropylene, fast plug speeds generally provide the best material distribution in the part.

The shaped laminate is then cooled in the mold. Sufficient cooling to maintain a mold temperature of 30° C. to 65° C. is desirable. The part is below 90° C. to 100° C. before ejection in one embodiment. For the good behavior in thermoforming, the lowest melt flow rate polymers are desirable. The shaped laminate is then trimmed of excess laminate material.

Blow molding is another suitable forming means, which includes injection blow molding, multi-layer blow molding, extrusion blow molding, and stretch blow molding, and is especially suitable for substantially closed or hollow objects, such as, for example, gas tanks and other fluid containers. Blow molding is described in more detail in, for example, CONCISE ENCYCLOPEDIA OF POLYMER SCIENCE AND ENGINEERING 90-92 (Jacqueline I. Kroschwitz, ed., John Wiley & Sons 1990).

In yet another embodiment of the formation and shaping process, profile co-extrusion can be used. The profile co-extrusion process parameters are as above for the blow molding process, except the die temperatures (dual zone top and bottom) range from 150° C.-235° C., the feed blocks are from 90° C.-250° C., and the water cooling tank temperatures are from 10° C.-40° C.

One embodiment of an injection molding process is described as follows. The shaped laminate is placed into the injection molding tool. The mold is closed and the substrate material is injected into the mold. The substrate material has a melt temperature between 200° C. and 300° C. in one embodiment, and from 215° C. and 250° C. and is injected into the mold at an injection speed of between 2 and 10 seconds. After injection, the material is packed or held at a predetermined time and pressure to make the part dimensionally and aesthetically correct. Typical time periods are from 5 to 25 seconds and pressures from 1,380 kPa to 10,400 kPa. The mold is cooled between 10° C. and 70° C. to cool the substrate. The temperature will depend on the desired gloss and appearance desired. Typical cooling time is from 10 to 30 seconds, depending on part on the thickness. Finally, the mold is opened and the shaped composite article ejected.

Likewise, molded articles may be fabricated by injecting molten polymer into a mold that shapes and solidifies the molten polymer into desirable geometry and thickness of molded articles. Sheets may be made either by extruding a substantially flat profile from a die, onto a chill roll, or alternatively by calendaring. Sheet will generally have a thickness of from 10 mils to 100 mils (254 μm to 2540 μm), although the sheets may be substantially thicker. Tubing or pipe may be obtained by profile extrusion for uses in medical, potable water, land drainage applications or the like. The profile extrusion process involves the extrusion of molten polymer through a die. The extruded tubing or pipe is then solidified by chill water or cooling air into a continuous extruded articles. The tubing will generally be in the range of from 0.31 cm to 2.54 cm in outside diameter, and have a wall thickness of in the range of from 254 μm to 0.5 cm. The pipe will generally be in the range of from 2.54 cm to 254 cm in outside diameter, and have a wall thickness of in the range of from 0.5 cm to 15 cm. Sheets made from an embodiment of the polymeric compositions described herein may be used to form containers. Such containers may be formed by thermoforming, solid phase pressure forming, stamping and other shaping techniques. Sheets may also be formed to cover floors or walls or other surfaces.

In an embodiment of the thermoforming process, the oven temperature is between 160° C. and 195° C., the time in the oven between 10 and 20 seconds, and the die temperature, typically a male die, between 10° C. and 71° C. The final thickness of the cooled (room temperature), shaped laminate is from 10 µm to 6000 µm in one embodiment, from 200 µm to 6000 µm in another embodiment, and from 250 µm to 3000 µm in yet another embodiment, and from 500 µm to 1550 µm in yet another embodiment, a desirable range being any combination of any upper thickness limit with any lower thickness limit.

In an embodiment of the injection molding process, wherein a substrate material in injection molded into a tool including the shaped laminate, the melt temperature of the substrate material is between 230° C. and 255° C. in one embodiment, and between 235° C. and 250° C. in another embodiment, the fill time from 2 to 10 seconds in one embodiment, from 2 to 8 seconds in another embodiment, and a tool temperature of from 25° C. to 65° C. in one embodiment, and from 27° C. and 60° C. in another embodiment. In a desirable embodiment, the substrate material is at a temperature that is hot enough to melt any tie-layer material or backing layer to achieve adhesion between the layers.

In yet another embodiment, the polymeric compositions described herein may be secured to a substrate material using a blow molding operation. Blow molding is particularly useful in such applications as for making closed articles such as fuel tanks and other fluid containers, playground equipment, outdoor furniture and small enclosed structures. In one embodiment of this process, the polymeric compositions described herein are extruded through a multi-layer head, followed by placement of the uncooled laminate into a parison in the mold. The mold, with either male or female patterns inside, is then closed and air is blown into the mold to form the part.

It will be understood by those skilled in the art that the steps outlined above may be varied, depending upon the desired result. For example, an extruded sheet of the compositions described herein may be directly thermoformed or blow molded without cooling, thus skipping a cooling step. Other parameters may be varied as well in order to achieve a finished composite article having desirable features.

Exemplary articles made using the polymeric compositions described herein include cookware, storageware, toys, medical devices, sterilizable medical devices, sterilization containers, sheets, crates, containers, packaging, wire and cable jacketing, pipes, geomembranes, sporting equipment, chair mats, tubing, profiles, instrumentation sample holders and sample windows, outdoor furniture (e.g., garden furniture) playground equipment, automotive, boat and water craft components, and other such articles. In particular, the compositions are suitable for automotive components such as bumpers, grills, trim parts, dashboards and instrument panels, exterior door and hood components, spoiler, wind screen, hub caps, mirror housing, body panel, protective side molding, and other interior and external components associated with automobiles, trucks, boats, and other vehicles. In particular, the polymeric compositions described herein are useful for producing "soft touch" grips in products such as personal care articles such as toothbrushes, etc.; toys; small appliances; packaging; kitchenware; sport & leisure products; consumer electronics; PVC and silicone rubber replacement medical tubing; industrial hoses; and shower tubing.

Film

The polymeric compositions described herein are also useful for the production of films. Methods for making the films of the polymeric compositions include those which are well known to those of ordinary skill in the art, including, but not limited to conventional tubular extrusion, or a blown bubble process, and cast extrusion. The extrusion temperatures, die temperatures, and chill roll temperatures are dependent on the composition employed, but will generally be within the following ranges for the compositions described herein: melt temperature, 170° C. to 250° C.; die temperature, 170° C. to 250° C.; and chill roll temperature, 10° C. to 65° C. The film-making process may also include embossing rolls to chill and form the film.

The films of the invention may have a layer adhered to one or both sides of the inventive film. The layers may be adhered by coextrusion of the inventive film with the optional additional layer or layers. In coextruded films, the individual layers are different in composition and retain their composition except at the interface layer. The optional additional layer may be, for example, a soft material such as an ethylene copolymer which may reduce the adhesive (i.e., sticky) feel of the inventive film. The optional additional layer may also be, for example, a thermoplastic. A thermoplastic layer may be used, for example, as a mechanical support for an elastic film to prevent sag, and as a barrier to adhesion of the polymer film to other surfaces. A thermoplastic layer may become a part of the integral use of an elastic film in that the composite film is stretched beyond the yield point of the thermoplastic layer, e.g., greater than 50% elongation, and allowed to retract due to the elastic forces of the elastic film. In this use, the thermoplastic film is wrinkled to yield a desirable surface finish of the composite elastic film. The thermoplastics that may be used for this purpose include, but are not limited to polypropylene and polyethylene.

In one embodiment, the mechanical properties, such as elastic recovery and stress relaxation, of films of the invention may be enhanced by thermal annealing and/or mechanical orientation.

Thermal annealing is conducted by maintaining the polymer blend or article made from the blend at a temperature between room temperature and 160° C. for a period of from 15 seconds to 7 days. A typical annealing period is 3 days at 50° C. or 5 minutes at 100° C. The annealing time and temperature can be adjusted for any particular blend composition by experimentation. It is believed that during this annealing process, there is intermolecular rearrangement of the polymer chains, leading to a material with greater recovery from tensile deformation than the unannealed material.

Mechanical orientation can be done by the temporary, forced extension of the blend along one or more axis for a short period of time before it is allowed to relax in the absence of extensional forces. It is believed that the mechanical orientation of the polymer leads to reorientation of the crystallizable portions of the blend. Orientation is conducted by maintaining the polymer blend or article made from the blend at an extension of 10% to 400% for a period of 0.1 seconds to 24 hours. A typical orientation is an extension of 200% for a momentary period (generally less than 1 minute) at room temperature.

Orientation of a film may be carried out in the machine direction (MD) or the transverse direction (TD) or both directions (biaxially) using conventional equipment and processes. For orientation in the MD, a polymeric film at an elevated temperature, but below the crystalline melting point of the polymer, is passed from a feed roll of film around two rollers driven at different surface speeds and finally to a take-up roller. The driven roller closest to the take-up roll is driven faster than the driven roller closest to the feed roll, such that the film is stretched between the driven rollers. The assembly may include a roller intermediate the second roller and take-up roller to cool the film. The second roller and the take-up roller may be driven at the same peripheral speeds to maintain the film in the stretched condition. If supplementary cooling is not used, the film will cool to ambient temperature on the take-up roller. The degree of stretch will depend on the relative peripheral speeds of the driven rollers and the distance between the rollers. Stretch rates of 50%/minute to 500%/minute will be satisfactory for most MD orientation applications.

For orientation in the TD, the film orientation is carried out in a tentering device. The film is cast or unwound from a film roll and then gripped by the edges for processing through the orientation steps. The film is passed successively through a preheat step, a stretching step at elevated temperatures (e.g., from 37° C. to a temperature slightly below the crystalline melting point of the ethylene crystallizable copolymer), an annealing step, and finally a cooling step. During the steps of preheating and stretching and a portion of the annealing step, the temperature is controlled at an elevated temperature, but below the crystalline melting point of the polymer. Tension may be maintained on the film during the annealing and cooling steps to minimize shrinkback. Upon cooling to ambient temperature, i.e., room temperature, or near ambient, the holding force may be released. The film may contract somewhat (snapback) in the TD, but will retain a substantial portion of its stretched length. The tenter operating conditions can vary within relatively wide ranges and will depend on the several variables including, for example, film composition, film thickness, degree of orientation desired, and annealing conditions.

As indicated earlier, the orientation process may include an annealing step. Annealing partially relieves the internal stress in the stretched film and dimensionally stabilizes the film for storage. Annealing may be carried out in a time and temperature dependent relationship.

In a particular process for film orientation, an interdigitating grooved roller assembly is used to simultaneously produce a desirable crinkled surface finish and orient the film. Such a process is described in U.S. Pat. No. 4,368,565. In this process, the film is stretched between two interlocking grooved rollers which are able to both biaxially stretch the film and orient it.

Experimental Evaluations

The following test methods and procedures were used in conducting experimental evaluations of various polymeric compositions as hereinafter described.

Test Methods

The heat of fusion of the polymers described herein was measured as follows. About 6 to 10 mg of a sheet of the polymer pressed at approximately 200° C. to 230° C. is removed with a punch die and annealed at room temperature for 24-48 hours. At the end of this period, the sample is placed in a Differential Scanning calorimeter (Perkin Elmer Pyris Analysis System) and cooled to about −50° C. to −70° C. The sample is heated at about 20° C./min to attain a final temperature of about 180° C. to 200° C. The thermal output is recorded as the area under the melting peak of the sample, which is typically at a maximum peak at about 30° C. to about 175° C. and occurs between the temperatures of about 0° C. and about 200° C. The thermal output is measured in Joules as a measure of the heat of fusion.

Tensile properties were measured by ASTM method D-412
Flexural Modulus was measured using ASTM method D-790
Tear strength was measured using ASTM method D-624
Hardness was measured using ASTM method D-2240
Vicat softening point was measured using ASTM method D-1525
Melt Flow Rate (MFR) and Melt Index were measured by ASTM method D-1238.
Density in g/cc is determined in accordance with ASTM 1505, based on ASTM D-1928, procedure C, plaque preparation.

Blends shown in examples were made by mixing all components, including the PPU component, the SBC component, the optional amounts of process oil and other ingredients in a Brabender intensive mixture for about 10 minutes at a temperature controlled to be within 185° C. and 220° C. At the end of the mixing, the mixture was removed and pressed out into a 15.24 cm×15.24 cm mold into a pad about 0.635 cm thick at 215° C. for 3 to 5 minutes. Films of about 3.3 mm thickness were pressed out at 200° C. for 3 to 5 minutes. At the end of this period, the pad was cooled and removed and allowed to anneal for 14 days at room temperature. Test specimens of the required geometry were removed from this pad and evaluated. Samples of thickness of about 0.2 mm, for tension set measurements, were prepared using the method outlined above.

Tension set was determined on the samples of the blend which had been extended to either 100% or 200% extension and then allowed to relax. The distance between crossheads corresponding to no change in load (or nominally zero load) was taken as length, L2. The original distance between the grips was the original length (L1) of the deformation zone. The tension set is given by the formula:

$$\text{Tension Set} = 100*(L2-L1)/L1.$$

The load loss is defined as the percentage decrease in stress at 50% strain of the loading and unloading cycles.

Experimental evaluations of comparative polymeric compositions and polymeric compositions exemplary of those described here were conducted. Table 1 lists the polymeric components used in one or more of the polymeric compositions evaluated with selected properties indicated. Included among the polymeric components listed are: (1) polymers comprising propylene-derived units (PPU's), (2) conventional polypropylene polymers, and (3) styrenic block copolymers.

TABLE I

| Polymeric Component | Type of Polymer | Mooney Viscosity ML (1 + 4) @ 125° C. | MFR @ 230° C. | $C_2$ wt % | Heat of Fusion (J/gm) | Triad Tacticity [mm] (%) |
|---|---|---|---|---|---|---|
| PPU1 | C2/C3 copolymer | 22 | | 15.8 | | ~90+ |
| PPU2 | C2/C3 copolymer | | 1.9 | 16.2 | 5.7 | ~90+ |
| PPU3 | C2/C3 copolymer | 25 | 3 | 16 | | ~90+ |
| PP 8013 L1 | Reactor made PP copolymer | | 8 | 17.5 | | |
| PP Borsoft ™ SD233CF | PP random heterophase copolymer | | 7 | | High | |
| PP Borsoft ™ SA233CF | PP random heterophase copolymer | | 0.8 | | High | |
| Exact ™ PX-5062 ("PX-5062") | Metallocene based PE | | 0.5* | | 58 | |

TABLE I-continued

| Polymeric Component | Type of Polymer | Mooney Viscosity ML (1 + 4) @ 125° C. | MFR @ 230° C. | C₂ wt % | Heat of Fusion (J/gm) | Triad Tacticity [mm] (%) |
|---|---|---|---|---|---|---|
| Escorene ™ 4292 ("ESC 4292") | polypropylene homopolymer | | 3 | | | |
| PP3155 | polypropylene homopolyme | | 36 | | | |
| Kraton ™ G1650 | SEBS | | <1** | | | |
| Kraton ™ G1655 | SEBS | | | | | |
| Kraton ™ G1657 | SEBS | | 22** | | | |
| Vector ™ 8508 D | SBS | | 10** | | | |
| Vector ™ 2518 | SBS | | 6§ | | | |
| Vector ™ 4461 | SBS | | 23** | | | |
| Vector ™ 7400 | SBS | | 18** | | | |
| Vector ™ 4111 | SIS | | 12** | | | |
| Vector ™ 4211 | SIS | | 13** | | | |
| Vector ™ 4411 | SIS | | 40** | | | |

*Measured at 190° C. with 2.16 kg loading
**Measured at 200° C. with 5 kg loading
§Measured at 200° C. with 10 kg loading, 0.1564 die
†See copending U.S. Pat. App. Ser. No. 10/474,594

PPU1, PPU2, and PPU3 are ethylene-propylene random copolymers having the weight percents of ethylene-derived units indicated in Table 1, and the balance of propylene-derived units, and can be prepared using the following procedure. Continuous polymerization was conducted in a 9 liter continuous flow stirred tank reactor using hexane as the solvent. The liquid full reactor had a residence time of 9 minutes and the pressure was maintained at 700 kPa. A mixed feed of hexane, ethylene, and propylene was pre-chilled to approximately −30° C. to remove the heat of polymerization. Solution of catalyst/activator in toluene and the scavenger in hexane were separately and continuously admitted into the reactor to initiate the polymerization. The reactor temperature was maintained between 35 and 50° C., depending on the target molecular weight. The feed temperature was varied, depending on the polymerization rate to maintain a constant reactor temperature. The polymerization rate was varied from 0.5 Kg/hr to 4 Kg/hr. Hexane at 30 Kg/hr was mixed with ethylene at 717 g/hr and propylene at 5.14 Kg/hr and fed to the reactor. The polymerization catalyst, dimethyl silyl bridged bis-indenyl Hafnium dimethyl activated 1:1 molar ratio with N',N'-Dimethyl anilinium-tetrakis (pentafluorophenyl)borate was introduced at the rate of at 0.0135 g/hr. A dilute solution of triisobutyl aluminum was introduced into the reactor as a scavenger of catalyst terminators: a rate of approximately 111 mole of scavenger per mole of catalyst was adequate for this polymerization. After five residence times of steady polymerization, a representative sample of the polymer produced in this polymerization was collected. The solution of the polymer was withdrawn from the top, and then steam distilled to isolate the polymer. The polymerization rate was measured at 3.7 Kg/hr. The polymer produced in this polymerization had an ethylene content of 14%, ML (1+4) 125° C. of 13.1 and had isotactic propylene sequences.

Variations in the composition of the polymer were obtained principally by changing the ratio of ethylene to propylene. Molecular weight of the polymer was varied by either changing the reactor temperature or by changing the ratio of total monomer feed rate to the polymerization rate. Dienes for terpolymerization were added to the mixed feed stream entering the reactor by preparing the diene in a hexane solution and metering it in the required volumetric amount.

PP 8013 L1, Exact™ PX-5062, Escorene™ 4292, and PP3155 are available from ExxonMobil Chemical Company of Houston, Tex.

PP Borsoft™ SD233CF and SA233CF are available from Borealis of Denmark.

Kraton™ G1650, G1655, and G1657 are available from Kraton Polymers of Houston, Tex.

Vector™ 8508D, 2518, 4461, 7400, 4111, 4211, and 4411 are available from Dexco Polymers LP of Houston, Tex.

Crodamide™ ER is Erucamide available from Croda of Edison, N.J.

Irganox™ B 215 is an antioxidant available from Ciba Specialty Chemicals.

Table II gives additional properties of several polymeric components used in one or more of the polymeric compositions evaluated.

TABLE II

| Examples | 1 | 2 | 3 | 4 | 5 | 6 | 7 | 8 | 9 |
|---|---|---|---|---|---|---|---|---|---|
| Polymer | PPU2 | Vector ™ 4211 | Vector ™ 4411 | Vector ™ 7400 | Vector ™ 4111 | Vector ™ 2518 | Vector ™ 4461 | Kraton ™ G1650 | Kraton ™ G1657 |
| MFR (230° C.) | 1.9 | 14.3 | 41.4 | 17.1 | 12.3 | 0.07 | 16.7 | 0.07 | 7.6 |
| MI (190° C.) | 0.9 | 2.5 | 7.2 | 6.0 | 2.9 | 0.05 | 5.9 | — | 1.5 |
| Density (gm/cm³) | 0.859 | 0.936 | 0.965 | 0.917 | 0.927 | 0.944 | 0.964 | 0.906 | 0.881 |
| Hardness | 63 | 60 | 81 | 51 | 41 | 75 | 88 | 73 | 51 |
| Flexural Modulus (MPa) | 13.78 | 8.67 | 207.73 | 6.84 | 2.75 | 7.37 | 337.7 | 29.96 | 3.16 |
| 100% Modulus (MPa) | 1.4 | 1.7 | 4.1 | 1.1 | 0.5 | 2.4 | 4.0 | 2.6 | 0.9 |
| Tensile Strength (MPa) | 7.7 | 5.9 | 11.9 | 3.1 | 3.8 | 11.2 | 16.2 | 24.0 | 6.9 |
| Elongation (%) | >2000 | 1180 | 1650 | 1035 | >2000 | 1690 | 1770 | 1700 | 1790 |
| Vicat Softening (° C.) | 48 | 82 | 88 | 64 | 68 | 94 | 80 | 111 | 71 |
| Permanent Set (%) As is | 7 | 7 | 8 | 7 | 7 | 14 | 10 | 10 | 7 |
| Permanent Set (%) Prestretched to 200% | 5 | 5 | 5 | 5 | 7 | 12 | 7 | 5 | 7 |

TABLE II-continued

| Examples | 1 | 2 | 3 | 4 | 5 | 6 | 7 | 8 | 9 |
|---|---|---|---|---|---|---|---|---|---|
| Load Loss (%) As is | 41 | 14 | 60 | 18 | 14 | 33 | 59 | 33 | 16 |
| Load Loss (%) Prestretched to 200% | 27 | 16 | 39 | 19 | 13 | 27 | 33 | 17 | 15 |

Formulations 10-12 set forth in Table III demonstrate the effect of adding conventional polypropylene to compositions incorporating the PPU1 polymeric component. The formulations were prepared by melt blending the polymeric components according to the procedure described previously.

TABLE III

| Examples | 10 | 11 | 12 |
|---|---|---|---|
| PPU 1 (wt %) | 90.0 | 65.0 | 40.0 |
| ESC 4292 (wt %) | 10.0 | 35.0 | 60.0 |
| Results | | | |
| MFR@230° C. | 3.88 | 3.07 | 0.86 |
| Shore D hardness | 25 | 42 | 63 |
| Vicat Soft (C.) | 56 | 78 | 154 |
| Tensile | | | |
| Strain at break % | 2740 | 2979 | 2397 |
| Stress at 100% elongation (MPa) | 2.79 | 6.44 | 13.53 |
| Stress at 500% elongation (MPa) | 6.19 | 11.73 | 1.45 |
| Hysterisis to 200% elongation | | | |
| New | | | |
| Total work to 200% elongation (Kg. 2.54 cm) | 5.26 | 13.1 | 29.89 |
| Work lost in cycle (%) | 50 | 78 | 90 |
| Tension set % | 6 | 18 | 61 |
| Oriented | | | |
| Total work to 200% elongation (lb. in) | 10.8 | 26.1 | 62.1 |
| Work lost in cycle (%) | 41 | 69 | 87 |
| Tension set % | 3 | 7 | 48 |

The data reported in Table III reveals that as the concentration of a conventional polypropylene component is increased in the polymeric compositions incorporating the PPU1 component, the Vicat softening of the polymeric compositions increases. Furthermore, the Hardness and stress at various strains also increase, indicative of a "stiffening" of the polymer compositions. However, as the Vicat softening point increases, the elasticity of the polymeric compositions, as determined by the tension set and hysteresis measurements, decrease.

Formulations 13-17 set forth in Table IV demonstrate the effect of adding various concentrations of conventional polypropylene to compositions incorporating the PPU2 polymeric component. The formulations were prepared by melt blending the polymeric components according to the procedure described previously.

TABLE IV

| Examples | 13 | 14 | 15 | 16 | 17 |
|---|---|---|---|---|---|
| PPU2 (wt %) | 95 | 90 | 85 | 80 | 75 |
| PP 3155 (wt %) | 5 | 10 | 15 | 20 | 25 |
| Results | | | | | |
| MFR (230° C) | 3.0 | 3.3 | 3.5 | 4.2 | 4.7 |
| MI (190° C) | 1.3 | 1.4 | 1.5 | 1.8 | 2.1 |
| Density (gm/cm³) | 0.8625 | 0.865 | 0.8666 | 0.8705 | 0.8725 |
| Hardness | 65 | 68 | 70 | 72 | 75 |
| Flexural Modulus (MPa) | 14.98 | 19.01 | 21.09 | 24.91 | 32.88 |
| 100% Modulus (MPa) | 1.75 | 1.96 | 1.99 | 2.46 | 3.27 |
| Tensile Strength (MPa) | 12.67 | 12.78 | 13.01 | 13.81 | 14.37 |
| Elongation (%) | 883 | 889 | 893 | 841 | 791 |
| Vicat Softening (° C) | 48 | 47 | 48 | 48 | 50 |
| Permanent Set (%) As is | 9 | 10 | 10 | 18 | |
| Permanent Set (%) Prestretched to 200% | 7 | 7 | 7 | 13 | |
| Load Loss (%) As is | 45 | 59 | 54 | 78 | |
| Load Loss (%) Prestretched to 200% | 29 | 33 | 43 | 66 | |

From the data reported in Table IV, it is observed that numerous physical properties of the polymeric compositions are affected by the inclusion of a conventional polypropylene component in the compositions. For example, as conventional polypropylene is added, density, hardness, flexural modulus, 100% modulus, tensile strength and Vicat softening point increase.

Formulations 18-25 set forth in Table V demonstrate polymeric compositions as described herein. The polymeric compositions incorporate PPU, SBC, and TPC polymeric components in accordance with the descriptions previously provided. Formulations 18-25 were prepared by melt blending the polymeric components according to the procedure described previously.

TABLE V

| Examples | 18 | 19 | 20 | 21 | 22 | 23 | 24 | 25 |
|---|---|---|---|---|---|---|---|---|
| PPU1 (wt %) | 65.0 | 40.0 | 46.7 | 25.0 | 56.7 | 38.0 | 10.0 | 25.0 |
| ESC 4292 (wt %) | 10.0 | 10.0 | 20.0 | 25.0 | 26.7 | 36.0 | 50.0 | 60.0 |
| Kraton G1655 (wt %) | 25 | 50 | 33.33 | 50 | 16.67 | 26 | 40 | 15 |
| Results | | | | | | | | |
| MFR @ 230° C. | 6.05 | 12.7 | 6.98 | 12.06 | 4.48 | 5.13 | 7.72 | 3.1 |
| Shore D hardness | 23 | 22 | 32 | 37 | 35 | 47 | 59 | 64 |
| Vicat Soft (° C.) | 56 | 59 | 64 | 81 | 64 | 120 | 152 | 156 |

TABLE V-continued

| Examples | 18 | 19 | 20 | 21 | 22 | 23 | 24 | 25 |
|---|---|---|---|---|---|---|---|---|
| Tensile | | | | | | | | |
| Strain at break % | 2300 | 2011 | 2629 | 1263 | 3258 | 2463 | 1865 | 2365 |
| Stress at 100% elongation (MPa) | 2.50 | 2.41 | 3.81 | 4.84 | 4.85 | 7.70 | 11.54 | 13.07 |
| Stress at 500% elongation (MPa) | 5.83 | 5.68 | 8.32 | 8.92 | 9.82 | 11.46 | 12.47 | 13.63 |
| New | | | | | | | | |
| Total work to 200% elongation (lb. in) | 9.3 | 8.6 | 14.1 | 19.8 | 19.4 | 31.5 | 59.1 | 64.9 |
| Work lost in cycle (%) | 46 | 46 | 60 | 73 | 67 | 82 | 92 | 91 |
| Tension set % | 4 | 3 | 6 | 10 | 9 | 23 | 74 | 75 |
| Oriented | | | | | | | | |
| Total work to 200% elongation (Kg. 2.54 cm) | 4.03 | 3.76 | 5.89 | 8.07 | 8.02 | 12.79 | 25.03 | 27.94 |
| Work lost in cycle (%) | 39 | 40 | 53 | 67 | 59 | 76 | 90 | 89 |
| Tension set (%) | 2 | 2 | 3 | 5 | 3 | 5 | 51 | 57 |

The data reported in Table V reveal that as the different polymeric component concentrations are varied, the elasticity of the polymeric compositions, as determined by the tension set measurement, can be maintained even over a wide range of other physical properties. Note that this was not possible with blends of PPU with conventional polypropylene. This effect is particularly pronounced by comparing Examples 21 and 22 in which tension set remains relatively unchanged as the Vicat softening point varies with variations in the polymeric composition components. Similarly, comparing Examples 18 and 20, it is revealed that even though the 100% modulus is substantially higher for Example 20, the elastic properties are essentially maintained.

Formulations 26-33 set forth in Table VI demonstrate polymeric compositions as described herein. The polymeric compositions incorporate PPU and SBC polymeric components in accordance with the descriptions previously provided. Formulations 26-33 were prepared by melt blending the polymeric components according to the procedure described previously.

centrations are varied in a two polymeric component blend, the elasticity of the polymeric compositions, as determined by the tension set measurement, is maintained. In particular, focusing on Examples 26-28, it is seen that the tension set values change insignificantly as the Vicat softening point, hardness, flexural modulus and tensile strength increase. It is seen again that in blends of PPU with conventional polypropylene, any increase in tensile strength, flexural modulus and Vicat softening point is accompanied by a decrease in elastic properties.

Maintenance of elastic properties is also reported in Table VII detailing Examples reporting the properties of other two polymeric component blends incorporating different SBC components than used in the Examples of Table VI. Formulations 34-41 were prepared by melt blending the polymeric components according to the procedure described previously. Conclusions similar to those drawn above can be made here as well. In Examples 34 to 37, the density, flexural modulus, hardness and Vicat Softening point, are all observed to

TABLE VI

| Examples | 26 | 27 | 28 | 29 | 30 | 31 | 32 | 33 |
|---|---|---|---|---|---|---|---|---|
| PPU2 (wt %) | 80 | 60 | 40 | 20 | 80 | 60 | 40 | 20 |
| Kraton ™ G1650 (wt %) | 20 | 40 | 60 | 80 | 0 | 0 | 0 | 0 |
| Kraton ™ G1657 (wt %) | 0 | 0 | 0 | 0 | 20 | 40 | 60 | 80 |
| Results | | | | | | | | |
| MFR (230° C.) | 1.0 | 0.6 | 0.3 | 0.1 | 2.5 | 3.7 | 4.9 | 5.7 |
| MI (190° C.) | 0.4 | 0.1 | 0.03 | 0.01 | 1.0 | 1.1 | 1.3 | 1.4 |
| Density (gm/cm$^3$) | 0.869 | 0.878 | 0.887 | 0.897 | 0.864 | 0.868 | 0.873 | 0.875 |
| Hardness | 62 | 63 | 66 | 70 | 58 | 56 | 54 | 51 |
| Flexural Modulus (MPa) | 12.49 | 13.85 | 17.50 | 18.92 | 10.75 | 8.11 | 5.70 | 5.0 |
| 100% Modulus (MPa) | 1.5 | 1.7 | 1.8 | 1.9 | 1.3 | 1.2 | 1.1 | 1.0 |
| Tensile Strength (MPa) | 10.4 | 14.9 | 20.2 | 19.8 | 7.6 | 7.5 | 7.9 | 8.0 |
| Elongation (%) | >2000 | >2000 | >2000 | 1790 | >2000 | >2000 | >2000 | >2000 |
| Vicat Softening (° C.) | 50 | 55 | 76 | 95 | 50 | 50 | 55 | 59 |
| Permanent Set (%) As is | 7 | 8 | 10 | 8 | 7 | 8 | 7 | 6 |
| Permanent Set (%) Prestretched to 200% | 7 | 7 | 7 | 7 | 4 | 4 | 5 | 4 |
| Load Loss (%) As Is | 37 | 38 | 37 | 37 | 34 | 31 | 29 | 27 |
| Load Loss (%) Prestretched to 200% | 25 | 24 | 24 | 23 | 24 | 22 | 20 | 19 |

Similar to the Examples 18-25, the data reported for Examples 26-33 reveal that as the polymeric component concentrations increase, the elastic behavior is, however, maintained in all the compositions.

TABLE VII

| Examples | 34 | 35 | 36 | 37 | 38 | 39 | 40 | 41 |
|---|---|---|---|---|---|---|---|---|
| PPU1 (wt %) | 80 | 60 | 40 | 20 | 80 | 60 | 40 | 20 |
| Vector ™ 2518 (wt %) | 20 | 40 | 60 | 80 | 0 | 0 | 0 | 0 |
| Vector ™ 4461 (wt %) | 0 | 0 | 0 | 0 | 20 | 40 | 60 | 80 |
| Results | | | | | | | | |
| MFR (230° C.) | 1.1 | 0.02 | 0.02 | | 2.5 | 4.5 | 7.4 | 9.9 |
| MI (190° C.) | 0.6 | 0.4 | 0.2 | 0.08 | 1.2 | 1.9 | 2.9 | 3.4 |
| Density (gm/cm$^3$) | 0.876 | 0.893 | 0.909 | 0.928 | 0.879 | 0.898 | 0.918 | 0.938 |
| Hardness | 62 | 66 | 70 | | 65 | 73 | 80 | 84 |
| Flexural Modulus (MPa) | 15.33 | 19.62 | 26.92 | | 16.70 | 46.07 | 100.85 | 194.52 |
| 100% Modulus (MPa) | 1.6 | 1.8 | 1.9 | 2.1 | 1.7 | 2.2 | 2.6 | 3.0 |
| Tensile Strength (MPa) | 7.0 | 8.8 | 9.5 | 10.3 | 8.8 | 10.3 | 11.3 | 12.9 |
| Elongation (%) | 1515 | >2000 | >2000 | >2000 | >2000 | >2000 | >2000 | >2000 |
| Vicat Softening (° C.) | 49 | 54 | 72 | 82 | 49 | 56 | 72 | 76 |
| Permanent Set (%) As is | 10 | 10 | 12 | 10 | 7 | 10 | 10 | 10 |
| Permanent Set (%) Prestretched to 200% | 4 | 5 | 7 | 7 | 5 | 7 | 7 | 7 |
| Load Loss (%) As is | 43 | 40 | 35 | 39 | 42 | 47 | 56 | 60 |
| Load Loss (%) Prestretched to 200% | 27 | 28 | 23 | 23 | 30 | 30 | 33 | 32 |

Tables VIII and IX report the properties for Examples 42-57. These formulations are additional two polymeric component compositions incorporating a PPU component and an SBC component. The formulations of Examples 42-57 were prepared by melt blending the polymeric components according to the procedure described previously.

In particular, Examples 42-57 demonstrates the maintenance of stable elastic properties in polymeric compositions with different SBC components.

TABLE VIII

| Examples | 42 | 43 | 44 | 45 | 46 | 47 | 48 | 49 |
|---|---|---|---|---|---|---|---|---|
| PPU 2 (wt %) | 80 | 60 | 40 | 20 | 80 | 60 | 40 | 20 |
| Vector ™ 7400 (wt %) | 20 | 40 | 60 | 80 | 0 | 0 | 0 | 0 |
| Vector ™ 4111 (wt %) | 0 | 0 | 0 | 0 | 20 | 40 | 60 | 80 |
| Results | | | | | | | | |
| MFR (230° C.) | 1.9 | 2.2 | 3.7 | 5.8 | 2.7 | 4.8 | 7.5 | 10.0 |
| MI (190° C.) | 1.0 | 1.2 | 1.6 | 2.2 | 1.2 | 1.9 | 2.1 | 2.5 |
| Density (gm/cm$^3$) | 0.871 | 0.882 | 0.893 | 0.905 | 0.873 | 0.886 | 0.899 | 0.912 |
| Hardness | 58 | 54 | 51 | 50 | 57 | 54 | 49 | 44 |
| Flexural Modulus (MPa) | 11.46 | 10.16 | 8.03 | 5.61 | 10.02 | 7.66 | 4.92 | 3.85 |
| 100% Modulus (MPa) | 1.3 | 1.0 | 1.0 | 0.9 | 1.3 | 1.1 | 0.8 | 0.6 |
| Tensile Strength (MPa) | 6.3 | 5.1 | 4.8 | 4.3 | 7.0 | 6.1 | 5.0 | 4.0 |
| Elongation (%) | >2000 | >2000 | >2000 | >2000 | >2000 | >2000 | >2000 | >2000 |
| Vicat Softening (° C.) | 47 | 46 | 49 | 60 | 48 | 48 | 50 | 57 |
| Permanent Set (%) As is | 8 | 10 | 10 | 7 | 7 | 9 | 7 | 10 |
| Permanent Set (%) Prestretched to 200% | 4 | 7 | 7 | 5 | 4 | 5 | 5 | 5 |
| Load Loss (%) As is | 38 | 34 | 30 | 27 | 34 | 28 | 21 | 18 |
| Load Loss (%) Prestretched to 200% | 26 | 27 | 23 | 22 | 23 | 22 | 19 | 16 |

TABLE IX

| Examples | 50 | 51 | 52 | 53 | 54 | 55 | 56 | 57 |
|---|---|---|---|---|---|---|---|---|
| PPU 2 (wt %) | 80 | 60 | 40 | 20 | 80 | 60 | 40 | 20 |
| Vector ™ 4211 (wt %) | 20 | 40 | 60 | 80 | 0 | 0 | 0 | 0 |
| Vector ™ 4411 (wt %) | 0 | 0 | 0 | 0 | 20 | 40 | 60 | 80 |
| Results | | | | | | | | |
| MFR (230° C.) | 3.2 | 5.1 | 8.4 | 9.8 | 4.4 | 9.1 | 25.5 | 24.9 |
| MI (190° C.) | 1.5 | 1.7 | 2.1 | 2.3 | 1.7 | 2.5 | 5.4 | 5.0 |
| Density (gm/cm$^3$) | 0.876 | 0.891 | 0.907 | 0.924 | 0.879 | 0.898 | 0.919 | 0.940 |
| Hardness | 61 | 60 | 59 | 57 | 66 | 72 | 79 | 82 |
| Flexural Modulus (MPa) | 11.81 | 11.27 | 7.85 | 8.23 | 16.14 | 29.35 | 94.18 | 218.5 |
| 100% Modulus (MPa) | 1.4 | 1.3 | 1.4 | 1.2 | 1.8 | 2.1 | 2.6 | 3.1 |
| Tensile Strength (MPa) | 7.5 | 7.3 | 7.2 | 7.0 | 8.7 | 9.7 | 10.7 | 11.4 |
| Elongation (%) | >2000 | >2000 | >2000 | >2000 | >2000 | >2000 | >2000 | >2000 |
| Vicat Softening (° C.) | 49 | 52 | 60 | 71 | 49 | 55 | 80 | 85 |

TABLE IX-continued

| Examples | 50 | 51 | 52 | 53 | 54 | 55 | 56 | 57 |
|---|---|---|---|---|---|---|---|---|
| Permanent Set (%) As is | 7 | 7 | 7 | 7 | 7 | 8 | 10 | 10 |
| Permanent Set (%) Prestretched to 200% | 4 | 3 | 3 | 4 | 4 | 4 | 5 | 4 |
| Load Loss (%) As is | 33 | 32 | 45 | 45 | 45 | 52 | 59 | 60 |
| Load Loss (%) Prestretched to 200% | 23 | 21 | 19 | 18 | 26 | 28 | 30 | 26 |

Example 58 to 60 reported in Table X illustrate formulations made by combinations of PPU3 with SBS and either a reactor PP copolymer (PP 8013 L1) or a random PP copolymer (PP Borsoft™ TM SA 233 CF) with a high level of a process mineral oil (Plastol 537) prepared by melt blending, showing low hardness with very high mechanical properties like tensile strength, elongation and tear strength without any oil exudation. Examples 61-62 and 65 of Table X illustrate formulations containing high wt. % of PPU combined with SBS and PP showing low hardness with very high mechanical properties like tensile strength, elongation and tear strength and excellent injection molding surface aspect without noticeable surface defects like flow and sink marks. Examples 63 and 64 of Table X illustrate formulations with combination of PPU3 and metallocene based PE (PX-5062) and SBS with PP showing low hardness with very high mechanical properties like tensile strength, elongation and tear strength excellent injection molding surface aspect without noticeable surface defects like flow and sink marks. Formulation 66 in Table X shows that a product with low hardness and excellent mechanical properties and acceptable MFR may be produced without the use of a process oil which should be avoided in order to meet impact and low fogging requirements in automotive interior applications.

Testing dumbbells for mechanical properties measurements reported in Table X were cut from injection molded plaques of 15 mm long, 10 mm wide, and 2 mm thick, measured either perpendicular or parallel or both to flow directions.

TABLE X

| | | | | | Examples | 58 | 59 | 60 | 61 | 62 | 63 | 64 | 65 | 66 |
|---|---|---|---|---|---|---|---|---|---|---|---|---|---|---|
| | | | | PP 8013 L1 | | 11 | — | 12 | 12 | — | — | — | — | 16 |
| | | | | PP Borsoft ™ SD 233 CF | | — | 12 | — | — | — | — | — | — | — |
| | | | | PP Borsoft ™ SA 233 CF | | — | — | — | — | 17 | 17 | 17 | 12 | — |
| | | | | PPU3 | | 36 | 44 | 44 | 65 | 60 | 30 | 40 | 65 | 61 |
| | | | | PX-5062 | | — | — | — | — | — | 30 | 20 | — | — |
| | | | | Vector 8508 D | | 11.65 | 14 | 14 | 17.7 | 17.7 | 17.7 | 17.7 | 17.7 | 17.7 |
| | | | | Omya ™ BL (CaCO3) | | 22 | 14.55 | 14.55 | — | — | — | — | — | 5 |
| | | | | Plastol ™ 537 | | 19 | 15 | 15 | 5 | 5 | 5 | 5 | 5 | — |
| | | | | Crodamide ™ ER | | 0.15 | 0.15 | 0.15 | — | — | — | — | — | — |
| | | | | Irganox ™ B 215 | | 0.2 | 0.3 | 0.3 | 0.3 | 0.3 | 0.3 | 0.3 | 0.3 | 0.3 |
| | | Total Test Speed/ | Specimen | | | 100 | 100 | 100 | 100 | 100 | 100 | 100 | 100 | 100 |
| Parameter | Method | Conditions | Size | Units | | | | | | | | | | |
| Melt Flow Rate | ISO 1133 | 230° C./ 2.16 kg | Pellets | g/10 min | | 12.3 | 8.5 | 7.5 | 3.2 | 2.5 | 1.8 | 2.0 | 2.7 | — |
| Hardness | ISO 868 | 15s delay | Disk 2 mm/50 mm (thickness./ diameter) | Sh A | | 60 | 64 | 65 | 62 | 67 | 65 | 67 | 62 | 76 |
| Density | ISO 1183 | — | Disk 2 mm/ 30 mm | g/cm$^3$ | | 1.038 | 0.976 | 0.976 | 0.882 | — | — | — | — | — |
| Properties @ RT | | | | | | Perp./ Par. | Perp. | Perp./ Par. | Perp. | Perp./ Par. | Perp./ Par. | Perp./ Par. | Perp. | Perp. |
| Tensile Strength | ISO 527-3 | 100 mm/min | | MPa | | 8.1/5.2 | 10.8 | 10.6/ 6.4 | 13.7/ 7.5 | 16.6/ 6.5 | 12.4/ 5.5 | 13.6/ 6.1 | 15.6/ 6.2 | 19.1/ 10.42 |
| Elongation at Break | ISO 527-3 | 100 mm/min | Type5 dumbbell 2 mm ISO plaque | % | | >1000/ 767 | >1000 | >1000/ 725 | >1000/ 722 | >1000/ 505 | 963/ 394 | >988/ 474 | 989/ 564 | 903/ 651 |
| Modulus @ 100% Strain | ISO 527-3 | 100 mm/min | | MPa | | 1.6/2.0 | 1.8 | 1.7/2.4 | 1.6/2.0 | 2.0/3.2 | 1.9 / 3.6 | 1.9/ 3.4 | 1.6 / 2.6 | 2.9/ 3.7 |
| Tear Strength | ISO 34-Ba | 500 mm/min | Angle/without nick 2 mm ISO plaque | kN/m | | 30 | 33 | 35 | 32 | 38 | 38 | 37 | 33 | 54 |

All patents and publications, including priority documents and testing procedures, referred to herein are hereby incorporated by reference in their entireties.

Although the present invention and its advantages have been described in detail, it should be understood that various changes, substitutions, and alterations could be made without departing from the spirit and scope of the invention as defined by the following claims.

The invention claimed is:
1. A polymeric composition comprising:
(i) from about 25 wt. % to about 65 wt. %, based on the total weight of the polymeric composition, of a polymer comprising at least 75 wt. % propylene-derived units and having a heat of fusion of less than 75 J/g and an isotactic triad fraction of from about 65% to about 99%;

(ii) from about 16 wt. % to about 50 wt. %, based on the total weight of the polymeric composition, of a styrenic block copolymer (SBC), wherein the SBC is selected from the group consisting of styrene-butadiene-styrene, styrene-ethylene/butylene-styrene, styrene-ethylene/propylene-styrene, styrene-isoprene-styrene, and mixtures thereof, and wherein the SBC is comprised of less than 20 wt % diblock segments and has a styrene content of about 10 to about 50 wt %, and the SBC has an MFR (230° C./5 kg) within the range of from about 0.1 to about 40 dg/min;

(iii) from about 10 wt % to about 36 wt. % of a propylene homopolymer or copolymer having an upper limit of 8 wt % of copolymer units selected from ethylene and $C_4$-$C_{12}$ alpha-olefins; and wherein the polymeric composition has a tension set from 200% elongation of less than 50% at 23° C. and wherein the weight percentages of polymer are additive to 100.0%.

2. The polymeric composition of claim 1 wherein the polymer comprising propylene-derived units comprises at least 5 wt. % of comonomer units derived from monomers other than propylene.

3. The polymeric composition of claim 2 wherein the comonomer units are ethylene-derived units.

4. The polymeric composition of claim 3 wherein the polymer comprising propylene-derived units comprises from about 75 wt. % to about 95 wt. % propylene-derived units and from about 5 wt. % to about 25 wt. % ethylene-derived units.

5. The polymeric composition of claim 4 having a Vicat softening point of at least 40° C.

6. The polymeric composition of claim 5 wherein the styrenic block copolymer has a melt flow rate of from 0.1 to 150.

7. The polymeric composition of claim 6 having a Vicat softening point of from 40° C. to 120° C.

8. The polymeric composition of claim 7 wherein the composition has a Shore D hardness of less than 50.

9. The polymeric composition of claim 7 wherein the combined weight of the polymer comprising propylene-derived units and the styrenic block copolymer is from about 60 wt. % to about 100 wt. % of the total weight of the polymeric composition.

10. The polymeric composition of claim 9 further comprising from about 2 wt. % to about 40 wt. % of an additional polymer comprising propylene-derived units, wherein said additional polymer comprising propylene-derived units has an isotactic triad fraction of from about 80% to about 98% and comprises at least 90 wt. % of propylene-derived units and from about 2 wt. % to about 10 wt. % of comonomer units derived from olefins other than propylene.

11. The polymeric composition of claim 9 wherein the polymer comprising propylene-derived units comprises from about 5 wt. % to about 20 wt. % of ethylene-derived units.

12. The polymeric composition of claim 9 comprising from about 1 wt. % to about 35 wt. % of an ethylene copolymer having a density of from about 0.85 to about 0.94 g/cm$^3$.

13. The polymeric composition of claim 9 comprising about 1 wt. % to about 15 wt. % of a tackifier resin.

14. The polymeric composition of claim 9 comprising from about 1 wt. % to about 60 wt. % of an additive selected from the group consisting of a filler, a pigment, a coloring agent, a processing oil, a plasticizer, and mixtures thereof.

15. The polymeric composition of claim 9 comprising from about 1 wt. % to about 95 wt. % of a non-functionalized plasticizer wherein the non-functionalized plasticizer has a kinematic viscosity of at least 2 cSt at 100° C.

16. The polymeric composition of claim 15 wherein the non-functionalized plasticizer has a flashpoint of at least 200° C.

17. The polymeric composition of claim 9 wherein the polymer comprising propylene-derived units comprises from about 10 wt. % to about 20 wt. % of ethylene-derived units.

18. The polymeric composition of claim 17 wherein the polymer comprising propylene-derived units has a Shore A hardness of less than about 90.

19. A polymeric composition comprising:
(a) from about 20 wt. % to about 65 wt. %, based on the total weight of the polymeric composition, of a polymer comprising at least 75 wt. % propylene-derived units and having a heat of fusion of from about 1 to about 75 J/g and an isotactic triad fraction of about 65% to about 99%; and
(b) from about 10 wt. % to about 18 wt. %, based on the total weight of the polymeric composition, of a styrenic block copolymer (SBC), wherein the SBC is selected from the group consisting of styrene-butadiene-styrene, styrene-ethylene/butylene-styrene, styrene-ethylene/propylene-styrene, styrene-isoprene-styrene, and mixtures thereof, and wherein the SBC is comprised of less than 20 wt % diblock segments and has a styrene content of about 10 to about 50 wt % and the SBC has an MFR (230° C./5 kg) within the range of from about 0.1 to about 40 dg/min;
(c) and one of:
(i) from about 11 wt % to about 16 wt % of a propylene copolymer having at least 2 wt % and an upper limit of 16 wt % copolymer units selected from ethylene and $C_4$-$C_{12}$ alpha-olefins, or
(ii) from about 10 wt % to 35 wt % of a copolymer of ethylene and propylene comprising 50 mol % or greater ethylene derived units;
(d) up to about 19 wt % of process oil by weight of the composition; and
(e) less than 30 wt % of an inorganic filler by weight of the composition;
wherein the polymeric composition has an MFR of from about 0.1 to about 40, a Shore A hardness of less than 80, a Vicat softening point of at least 40° C., and a tension set from elongation of 200% of less than 50% at 23° C. a tensile strength of at least 4 MPa and less than about 40 MPa.

20. A film, fabric, fiber or article comprising the polymeric composition of claim 19.

21. The polymeric composition of claim 19 having a tension set from elongation of 200% of less than 25% at 23° C.

22. The polymeric composition of claim 19 wherein the polymer comprising propylene-derived units has an isotactic triad fraction of from about 50% to about 98%, an MFR of from about 0.5 to about 200, a heat of fusion of less than 60 J/g.

23. The polymeric composition of claim 22 wherein the polymer comprising propylene-derived units is a copolymer comprising at least 75 wt. % of propylene-derived units and from about 5.0 wt. % to about 25.0 wt. % of ethylene-derived units.

24. The polymeric composition of claim 23 wherein polymer comprising propylene-derived units further comprises polyene-derived units in an amount within the range of from about 0.3 wt. % to about 3 wt. %, based on the combined weight of the propylene-derived units and the ethylene-derived units.

25. The polymeric composition of claim 24 wherein the polyene-derived units are derived from 5-ethylidene-2-norbornene.

26. The polymeric composition of claim 25 wherein the polyene-derived units are present in an amount within the range of from about 1 wt. % to about 3 wt. %, based on the combined weight of the propylene-derived units and the ethylene-derived units.

27. The polymeric composition of claim 24 wherein the polyene-derived units are derived from 5-vinyl-2-norbornene.

28. The polymeric composition of claim 27 wherein the polyene-derived units are present in an amount within the range of from about 0.5 wt. % to about 1.5 wt. %, based on the combined weight of the propylene-derived units and the ethylene-derived units.

29. The polymeric composition of claim 23 wherein at least 10 wt. % of the polymer comprising propylene-derived units is crosslinked.

30. The polymeric composition of claim 29 wherein the polymeric composition of claim 29 is crosslinked to a degree such that the viscosity ratio of the polymeric composition is from 1.2 to 10.

31. A film comprising a polymeric composition, the polymeric composition comprising:
 (i) from about 25 wt. % to about 65 wt. %, based on the total weight of the polymeric composition, of a polymer comprising at least 75 wt. % propylene-derived units and having a heat of fusion of less than 75 J/g and an isotactic triad fraction of from about 65% to about 99%;
 (ii) from about 16 wt. % to about 50 wt. %, based on the total weight of the polymeric composition, of a styrenic block copolymer (SBC), wherein the SBC is selected from the group consisting of styrene-butadiene-styrene, styrene-ethylene/butylene-styrene, styrene-ethylene/propylene-styrene, styrene-isoprene-styrene, and mixtures thereof, and wherein the SBC is comprised of less than 20 wt % diblock segments and has a styrene content of about 10 to about 50 wt %, and the SBC has an MFR (230° C./5 kg) within the range of from about 0.1 to about 40 dg/min;
 (iii) from about 10 wt % to about 36 wt. % of a propylene homopolymer or copolymer having an upper limit of 8 wt % of copolymer units selected from ethylene and $C_4$-$C_{12}$ alpha-olefins; and
 wherein the polymeric composition has a tension set from 200% elongation of less than 50% at 23° C. and wherein the weight percentages of polymer are additive to 100.0%.

32. The film of claim 31 wherein the polymer comprising propylene-derived units comprises at least 5 wt. % of comonomer units derived from monomers other than propylene.

33. The film of claim 32 wherein the comonomer units are ethylene-derived units.

34. The film of claim 33 wherein the polymer comprising propylene-derived units comprises from about 75 wt. % to about 95 wt. % propylene-derived units and from about 5 wt. % to about 25 wt. % ethylene-derived units.

35. The film of claim 34 wherein the polymeric composition has a Vicat softening point of at least 40° C.

36. A fabric comprising a polymeric composition, the polymeric composition comprising:
 (i) from about 25 wt. % to about 65 wt. %, based on the total weight of the polymeric composition, of a polymer comprising at least 75 wt. % propylene-derived units and having a heat of fusion of less than 75 J/g and an isotactic triad fraction of from about 65% to about 99%;
 (ii) from about 16 wt. % to about 50 wt. %, based on the total weight of the polymeric composition, of a styrenic block copolymer (SBC), wherein the SBC is selected from the group consisting of styrene-butadiene-styrene, styrene-ethylene/butylene-styrene, styrene-ethylene/propylene-styrene, styrene-isoprene-styrene, and mixtures thereof, and wherein the SBC is comprised of less than 20 wt % diblock segments and has a styrene content of about 10 to about 50 wt %, and the SBC has an MFR (230° C./5 kg) within the range of from about 0.1 to about 40 dg/min;
 (iii) from about 10 wt % to about 36 wt. % of a propylene homopolymer or copolymer having an upper limit of 8 wt % of copolymer units selected from ethylene and $C_4$-$C_{12}$ alpha-olefins; and
 wherein the polymeric composition has a tension set from 200% elongation of less than 50% at 23° C. and wherein the weight percentages of polymer are additive to 100.0%.

37. The fabric of claim 36 wherein the polymer comprising propylene-derived units comprises at least 5 wt. % of comonomer units derived from monomers other than propylene.

38. The fabric of claim 37 wherein the comonomer units are ethylene-derived units.

39. The fabric of claim 38 wherein the fabric is a nonwoven fabric and wherein the polymer comprising propylene-derived units comprises from about 75 wt. % to about 95 wt. % propylene-derived units and from about 5 wt. % to about 25 wt. % ethylene-derived units.

40. The fabric of claim 39 wherein the polymeric composition has a Vicat softening point of at least 40° C.

41. A fiber comprising a polymeric composition, the polymeric composition comprising:
 (i) from about 25 wt. % to about 65 wt. %, based on the total weight of the polymeric composition, of a polymer comprising at least 75 wt. % propylene-derived units and having a heat of fusion of less than 75 J/g and an isotactic triad fraction of from about 65% to about 99%;
 (ii) from about 16 wt. % to about 50 wt. %, based on the total weight of the polymeric composition, of a styrenic block copolymer (SBC), wherein the SBC is selected from the group consisting of styrene-butadiene-styrene, styrene-ethylene/butylene-styrene, styrene-ethylene/propylene-styrene, styrene-isoprene-styrene, and mixtures thereof, and wherein the SBC is comprised of less than 20 wt % diblock segments and has a styrene content of about 10 to about 50 wt %, and the SBC has an MFR (230° C./5 kg) within the range of from about 0.1 to about 40 dg/min;
 (iii) from about 10 wt % to about 36 wt. % of a propylene homopolymer or copolymer having an upper limit of 8 wt % of copolymer units selected from ethylene and $C_4$-$C_{12}$ alpha-olefins; and
 wherein the polymeric composition has a tension set from 200% elongation of less than 50% at 23° C. and wherein the weight percentages of polymer are additive to 100.0%.

42. The fiber of claim 41 wherein the polymer comprising propylene-derived units comprises at least 5 wt. % of comonomer units derived from monomers other than propylene.

43. The fiber of claim 42 wherein the comonomer units are ethylene-derived units.

44. The fiber of claim 43 wherein the polymeric composition has a Vicat softening point of at least 40° C.

45. The fiber of claim 44 wherein the polymer comprising propylene-derived units has a heat of fusion of from about 1 J/g to about 75 J/g.

46. An article of commerce comprising a polymeric composition, the polymeric composition comprising:
 (i) from about 25 wt. % to about 65 wt. %, based on the total weight of the polymeric composition, of a polymer comprising at least 75 wt. % propylene-derived units and having a heat of fusion of less than 75 J/g and an isotactic triad fraction of from about 65% to about 99%;
 (ii) from about 16 wt. % to about 50 wt. %, based on the total weight of the polymeric composition, of a styrenic block copolymer (SBC), wherein the SBC is selected from the group consisting of styrene-butadiene-styrene, styrene-ethylene/butylene-styrene, styrene-ethylene/propylene-styrene, styrene-isoprene-styrene, and mixtures thereof, and wherein the SBC is comprised of less than 20 wt % diblock segments and has a styrene content of about 10 to about 50 wt %, and the SBC has an MFR (230° C./5 kg) within the range of from about 0.1 to about 40 dg/min;

(iii) from about 10 wt % to about 36 wt. % of a propylene homopolymer or copolymer having an upper limit of 8 wt % of copolymer units selected from ethylene and $C_4$-$C_{12}$ alpha-olefins; and wherein the polymeric composition has a tension set from 200% elongation of less than 50% at 23° C. and wherein the weight percentages of polymer are additive to 100.0%;

and wherein the article of commerce is selected from the group consisting of a garment, a sheet, a molded object, an extruded form, and a thermoformed article.

47. The article of commerce of claim 46 wherein the polymer comprising propylene-derived units comprises at least 5 wt. % of comonomer units derived from monomers other than propylene.

48. The article of commerce of claim 47 wherein the comonomer units are ethylene-derived units.

49. The article of commerce of claim 48 wherein the polymer comprising propylene-derived units comprises from about 75 wt. % to about 95 wt. % propylene-derived units and from about 5 wt. % to about 25 wt. % ethylene-derived units.

50. The article of commerce of claim 49 wherein the polymeric composition has a Vicat softening point of at least 40° C.

* * * * *